United States Patent
Goure et al.

(10) Patent No.: US 9,176,151 B2
(45) Date of Patent: *Nov. 3, 2015

(54) ANTIBODIES, KIT AND METHOD FOR DETECTING AMYLOID BETA OLIGOMERS

(75) Inventors: William F. Goure, Livermore, CA (US); Renee C. Gaspar, West Point, PA (US); Alexander McCampbell, Andover, MA (US); Mary J. Savage, West Point, PA (US); Paul J. Shughrue, South San Francisco, CA (US); Fubao Wang, Hopkinton, MA (US); Weirong Wang, New Brunswick, NJ (US); Abigail L. Wolfe, Ambler, PA (US); Nigyan Zhang, Houston, TX (US); Wei-Qin Zhao, Bethesda, MD (US)

(73) Assignee: Acumen Pharmaceuticals, Inc., Livermore, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/544,600

(22) Filed: Jul. 9, 2012

(65) Prior Publication Data

US 2013/0130288 A1 May 23, 2013

Related U.S. Application Data

(63) Continuation-in-part of application No. PCT/US2011/043866, filed on Jul. 13, 2011.

(60) Provisional application No. 61/364,210, filed on Jul. 14, 2010, provisional application No. 61/507,332, filed on Jul. 13, 2011.

(51) Int. Cl.
C07K 16/18 (2006.01)
G01N 33/532 (2006.01)
G01N 33/68 (2006.01)

(52) U.S. Cl.
CPC ............ *G01N 33/6896* (2013.01); *C07K 16/18* (2013.01); *C07K 2317/24* (2013.01); *C07K 2317/55* (2013.01); *C07K 2317/76* (2013.01); *C07K 2317/92* (2013.01); *C07K 2317/94* (2013.01); *G01N 2333/4709* (2013.01)

(58) Field of Classification Search
None
See application file for complete search history.

(56) References Cited

U.S. PATENT DOCUMENTS

| 7,780,963 | B2 | 8/2010 | Acton et al. | 424/133.1 |
| 7,811,563 | B2 | 10/2010 | Acton et al. | 424/133.1 |
| 2008/0025988 | A1* | 1/2008 | Yamaguchi et al. | 424/152.1 |
| 2008/0175835 | A1* | 7/2008 | Acton et al. | 424/130.1 |
| 2009/0035307 | A1* | 2/2009 | Barghorn et al. | 424/133.1 |
| 2010/0209434 | A1* | 8/2010 | Bishop et al. | 424/158.1 |
| 2011/0008339 | A1 | 1/2011 | Yamaguchi et al. | 424/133.1 |

FOREIGN PATENT DOCUMENTS

| WO | WO 2006/055178 | 5/2006 |
| WO | WO 2007/050359 | 5/2007 |
| WO | WO 2009055442 A1 * | 4/2009 |
| WO | WO 2012/009442 | 1/2012 |

OTHER PUBLICATIONS

Lambert MP et al. (2007) Monoclonal antibodies that target pathological assemblies of Abeta. J. Neurochem. 100:23-35.*
Ying et al. (Feb. 2009) Preparation and characterization of a monoclonal antibody with high affinity for soluble Abeta oligomers. Hybridoma, 28(5):349-354.*
Zhao et al. "High Throughput Monitoring of Amyloid-Beta$_{42}$ Assembly into Soluble Oligomers Achieved by Sensitive Conformation State-Dependent Immunoassays" Journal of Alzheimer's Disease 2011 25:655-669.
International Search Report from PCT/US2012/045956, Jan. 2, 2013, WO.
Fukumoto et al. "High-Molecular-Weight β-Amyloid Oligomers are Elevated in Cerebrospinal Fluid of Alzheimer Patients" The FASEB Journal 2010 24:2716-2726.
Gandy et al. "Days-to-Criterion as an Indicator of Toxicity Associated with Human Alzheimer Amyloid-β Oligomers" Annals of Neurology 2010 68(2):220-230.
Gao et al. "Aβ40 Oligomers Identified as a Potential Biomarker for the Diagnosis of Alzheimer's Disease" PLoS One 2010 5(12):e15725.
Georganopoulou et al. "Nanoparticle-Based Detection in Cerebral Spinal Fluid of a Soluble Pathogenic Biomarker for Alzheimer's Disease" Proceedings of the National Academy of Sciences 2005 102(7):2273-2276.
Horikoshi et al. "Development of Aβ Terminal End-Specific Antibodies and Sensitive ELISA for Aβ Variant" Biochemical and Biophysical Research Communications 2004 319:733-737.
Tanghe et al. "Pathological Hallmarks, Clinical Parallels, and Value for Drug Testing in Alzheimer's Disease of the APP[V717I] London Transgenic Mouse Model" International Journal of Alzheimer's Disease 2010 2010:417314.
Xia et al. "A Specific Enzyme-Linked Immunosorbent Assay for Measuring β-Amyloid Protein Oligomers in Human Plasma and Brain Tissue of Patients With Alzheimer Disease" Archives of Neurology 2009 66(2):190-199.

* cited by examiner

*Primary Examiner* — Kimberly A Ballard
(74) *Attorney, Agent, or Firm* — Licata & Tyrrell P.C.

(57) ABSTRACT

This invention is a selective Aβ oligomer kit and immunoassay method capable of reliably and sensitively detecting Aβ oligomers in a biological sample of a patient. In one embodiment the inventive assay uses a pair of anti-Aβ oligomer antibodies, as capture and detection antibodies, to detect and quantify Aβ oligomers. The method can be used to differentiate Alzheimer's disease (AD) patients from non-AD patients and/or to stratify AD patients according to the severity of their disease.

13 Claims, 12 Drawing Sheets

Aβ Oligomer Sandwich ELISA

Pharmacodynamic Assay

Aβ Oligomer/Antibody Sandwich ELISA

Target Engagement Assay

ANTIBODIES, KIT AND METHOD FOR DETECTING AMYLOID BETA OLIGOMERS

INTRODUCTION

This application claims priority to U.S. Provisional Patent Application Ser. No. 61/507,332 filed Jul. 13, 2011, and is a continuation-in part application of PCT/US2011/043866, filed Jul. 13, 2011, which claims the benefit of priority from U.S. Provisional Patent Application Ser. No. 61/364,210, filed Jul. 14, 2010, the contents of which are incorporated herein by reference in their entireties.

BACKGROUND OF THE INVENTION

Alzheimer's disease (AD) is a devastating neurodegenerative disease characterized by amyloid β (Aβ) plaque accumulation in brain regions involved in learning and memory. While these large insoluble plaques were once thought to cause AD, evidence now indicates that small diffusible oligomers of Aβ may be responsible. Amyloid-derived diffusible ligands (ADDLs) are a species of Aβ oligomers that can be generated in vitro with properties similar to endogenous Aβ oligomers (U.S. Pat. No. 6,218,506; Klein, et al. (2004) *Neurobiol. Aging* 25:569-580; Lambert, et al. (1998) *Proc. Natl. Acad. Sci. USA* 95:6448-6453). Aβ oligomers are present in the brain of AD patients, they bind neurons, and they induce deficits in neuronal morphology and memory. Studies with antibodies that bind Aβ oligomers have shown improvement in both neuronal morphology and memory.

Assays to measure Aβ monomers are known. For example, a sandwich ELISA composed of N-terminus (Aβ1) end-specific antibody (clone 82E1) and C-termini end-specific antibodies for Aβ1-40 (clone 1A10) and Aβ1-42 (clone 1C3) was developed to detect full-length Aβ1-40 and Aβ1-42 with a sensitivity in the sub-single digit fmol/ml (equivalent to single digit pg/ml) range with no cross-reactivity to APP (Horikoshi, et al. (2004) *Biochem. Biophys. Res. Commun.* 319:733-737 and US Patent Publication No. 2011/0008339). Additional assays have used the activity of β- and γ-secretase enzymes on the amyloid precursor protein (APP) to detect monomers; however, few assays have been reported that specifically and reliably detect Aβ oligomers in a human fluid sample, such as cerebrospinal fluid (CSF), in both normal control and in AD (Georganopoulou, et al. (2005) *Proc. Natl. Acad. Sci. USA* 102:2273-2276; Fukumoto, et al. (2010) *FASEB J.* 24:2716-2726; Gao, et al. (2010) *PLoS One* 5(12): e15725). Reported Aβ oligomer assays have employed a number of approaches, including ADDL-specific antibodies coupled with a bio-barcode PCR amplification platform (Georganopoulou, et al. (2005) supra), overlapping epitope ELISAs (Gandy, et al. (2010) *Ann. Neurol.* 68:220-230; Xia, et al. (2009) *Arch. Neurol.* 66:190-199), also paired first with size exclusion chromatography (Fukomoto, et al. (2010) supra), and amyloid-affinity matrices methods (Gao, et al. (2010) supra; Tanghe, et al. (2010) *Int. J. Alz. Dis.* 2010: 417314), followed by oligomer dissociation and measurement with antibodies to Aβ monomers.

Aβ oligomers have also been detected from either CSF or brain using gel electrophoresis followed by western blot analysis (Klyubin, et al. (2008) *J. Neurosci.* 28:4231-4237; Hillen, et al. (2010) *J. Neurosci.* 30:10369-10379), or subsequent to size exclusion chromatography (Shankar, et al. (2011) *Methods Mol. Biol.* 670:33-44), relying on the molecular weight of oligomers that are maintained after the electrophoretic procedure. However, electrophoretic and blotting techniques do not provide the sensitivity required to see these species in normal control CSF (Klyubin, et al. (2008) supra), which exhibit a 1000-fold range of Aβ oligomer concentrations (Georganopoulou, et al. (2005) supra). Aβ oligomer species represent a wide range of molecular weights and, as such, assignment of a precise molarity is problematic. While a lower limit of detection at 100 aM has been shown (Georganopoulou, et al. (2005) supra), most reported methods (Georganopoulou, et al. (2005) supra; Gao, et al. (2010) supra; Fukumoto, et al. (2010) supra; Gandy, et al. (2010) supra) do not assess selectivity between signals from Aβ oligomers as compared to Aβ monomers, so the concentrations noted should be viewed with caution. One assay (Xia, et al. (2009) *Arch. Neurol.* 66:190-199), marketed by Immunobiological Laboratories, Inc. (Minneapolis, Minn.) claims 320-fold selectivity for Aβ1-16 dimers as compared to Aβ40 monomer, but lacks the selectivity needed to avoid cross-reactivity with Aβ monomer in the CSF. As Aβ oligomers in the CSF are hypothesized to be present at fM levels and CSF Aβ monomers are present between 1.5-2 nM, an assay that selectively measures Aβ oligomers in a CSF sample must have exceptional selectivity for Aβ oligomers over monomers.

Aβ oligomers have also been used as a target for therapeutic monoclonal antibodies to treat AD (see, for example, U.S. Pat. Nos. 7,811,563, 7,780,963, and 7,731,962). It is believed that these antibodies access the central nervous system (CNS) and clear the toxic ADDL species from the brain, through 1) catalytic turnover by Fc-mediated activation of microglia, 2) clearance of antibody/ADDL complexes into the cerebrovasculature, or 3) enzymatic digestion of the ADDLs following antibody binding and improved access of degradative enzymes, such as neprilysin, insulin-degrading enzyme, plasmin, endothelin-converting enzymes (ECE-1 and -2), matrix metalloproteinases (MMP-2, -3 and -9), and angiotensin-converting enzyme (ACE). Thus, a goal of a selective Aβ oligomer assay is to measure the pharmacodynamic (PD) change in CNS Aβ oligomers following treatment with an anti-oligomer antibody or other treatment that alters Aβ monomer/oligomer formation or clearance. Additionally, an assay that would specifically enable the detection of Aβ oligomers bound to an anti-Aβ oligomer antibody, i.e., a target engagement (TE) assay, would be invaluable for the assessment of the therapeutic antibody following treatment.

SUMMARY OF THE INVENTION

The present invention is directed to a selective Aβ oligomer kit and method capable of reliably and sensitively detecting Aβ oligomers in a biological sample, e.g., a fluid sample, of a subject. The inventive kit and method use a pair of highly selective anti-Aβ oligomer antibodies to detect and quantify Aβ oligomers in a biological sample. In particular, the kit and method of the invention employ a capture antibody that (i) recognizes an N-terminal linear epitope of amyloid beta 1-42 peptide, e.g., an epitope within residues 1-20 of amyloid beta 1-42, (ii) recognizes a conformational epitope of amyloid beta 1-42 oligomers, (iii) has a higher affinity for amyloid beta 1-42 oligomers than for amyloid beta 1-42 monomer, amyloid beta 1-40 monomer, plaques and amyloid beta fibrils, (iv) exhibits less than a 10-fold decrease in $EC_{50}$ when stored at 40° C. for 1 month; and a detection antibody that recognizes an N-terminal linear epitope of amyloid beta 1-42 peptide, e.g., an epitope within residues 1-20 of amyloid beta 1-42. In some embodiments, the affinity of the capture antibody for amyloid beta 1-42 oligomers compared to amyloid beta 1-40 monomers in a competitive binding assay is at least 500:1. In other embodiments, the affinity of the capture antibody for amyloid beta 1-42 oligomers compared to amyloid beta 1-42 monomers in a sandwich ELISA assay is at least 500:1 or at least 1000:1. In still other embodiments, the capture antibody is a variant of antibody h3B3 or a variant of antibody 19.3. In certain embodiments, the detection antibody is 6E10, BAM-10, W0-2, 26D6, 2A10, 2B4, 4C2, 4E2, 2H4, 20C2, 2D6, 5F10, 1F4, 1F6, 2E12, 3B3 or 82E1, and can optionally include a label. Using the kit and method, optionally in combination with a means for concentrating an antibody-antigen complex, the level of detection of amyloid beta 1-42 oligomers is less than 5 pg/mL or less than 3 pg/mL. Isolated antibodies, or antibody fragments, of use in the kit and method of the invention are also provided.

BRIEF DESCRIPTION OF THE DRAWINGS

FIG. 6B) or Thr33 (N33T; FIG. 6C). Substitution of Asn33 with either S33 or T33 resulted in improved antibody stability versus the parental 19.3 antibody.

FIG. 7A shows the anti-Aβ oligomer antibody 19.3 as the capture antibody and 82E1 as the detection antibody over a range of Aβ oligomer concentrations. FIGS. 7B and 7C depict 6E10 and 19.3, respectively, as both the capture and detection antibodies. The 19.3×82E1 sandwich ELISA pair (FIG. 7A) was significantly more sensitive in detecting A3 oligomers as compared to other pairs (FIGS. 7B and 7C).

FIG. 10A shows that the Aβ oligomers levels were four-fold higher in AD patients as compared to age matched control, i.e., non-AD, patients in a blinded evaluation using the method herein. The differences were statistically significant to p≤0.0004 as determined using a two-way t-test and Mann Whitney analysis of ranks, assuming the population was non-Gaussian. FIG. 10B shows that the Aβ oligomer levels were eight-fold higher in AD patients as compared to young control, i.e., non-AD, patients in a blinded evaluation using the method herein. The differences were also statistically significant between these groups using the same statistical method as in FIG. 10A to a p-value≤0.0021.

FIG. 11A shows the reduced levels of Aβ1-42 monomer in the AD CSF samples. The differences were statistically significant to p≤0.002 as determined using a two-way t-test and Mann Whitney analysis of ranks, assuming the population was non-Gaussian. FIG. 11B shows the unchanged levels between the two groups of Aβ1-40 monomer.

FIG. 14A is a representation of anti-Aβ oligomer antibody 19.3/A3 oligomer complexes formed ex vivo with spiking into human CSF (circle) or casein buffer (triangle). FIG. 14B is a representation of anti-Aβ oligomer antibody 19.3/Aβ oligomer complexes formed ex vivo with spiking into human CSF (circle) or Casein buffer (triangle). Differential sensitivity was observed in the detection of 19.3/Aβ oligomer complexes in an anti-human kappa chain (capture)×82E1 (detection) target engagement ELISA. The anti-kappa capture antibody poorly differentiated the anti-Aβ oligomer antibody 19.3 from the endogenous antibody species in human CSF.

DETAILED DESCRIPTION OF THE INVENTION

Figure 1:
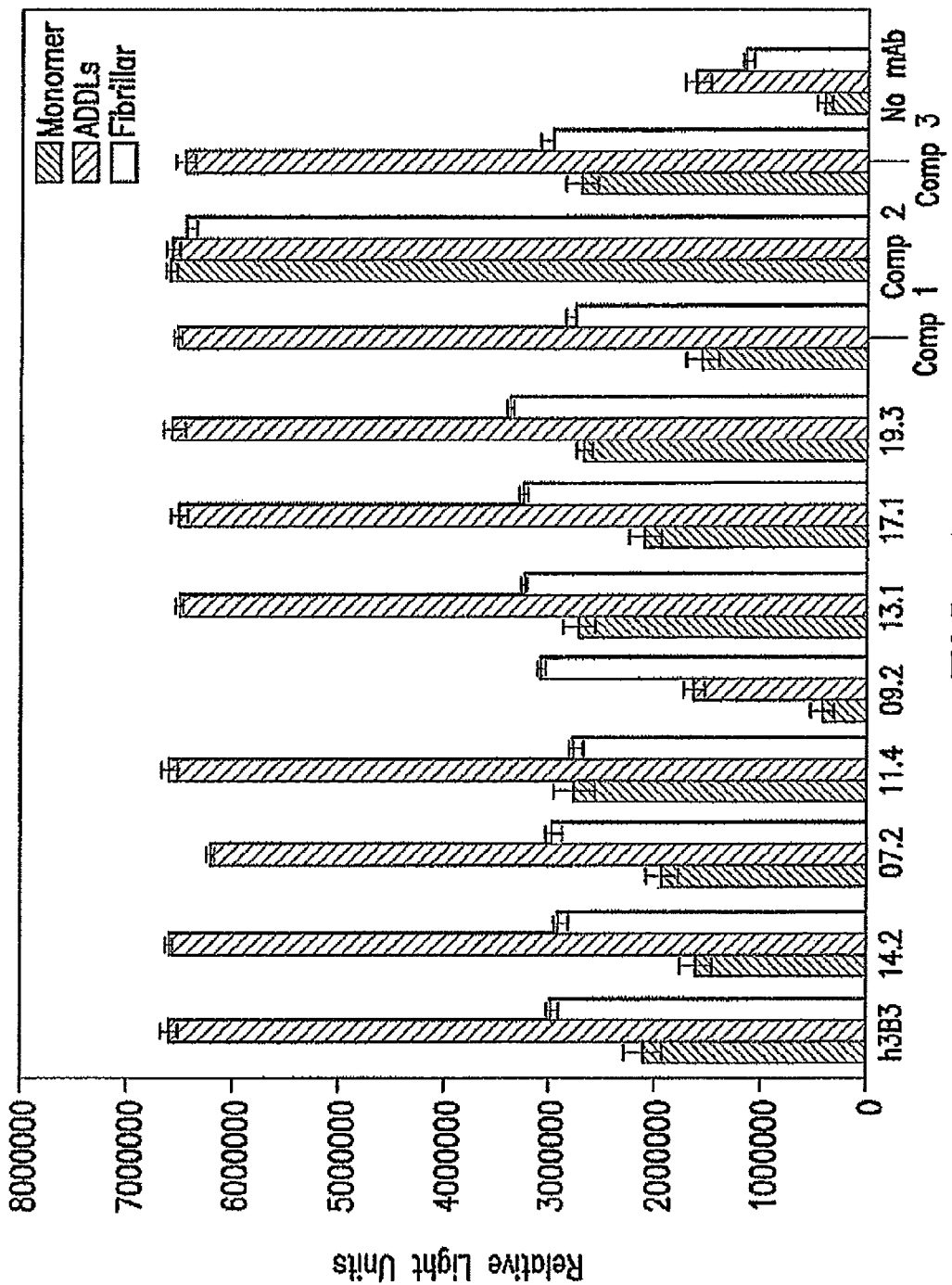
FIG. 1 is a graphic representation showing the selectivity of the anti-ADDL antibodies binding to the ADDL species of Aβ oligomers (middle bar of each set), as compared to Aβ monomer or Aβ fibril. Shown is ELISA binding of a panel of humanized (h3B3) and affinity matured anti-ADDL (14.2, 7.2, 11.4, 9.2, 13.1, 17.1, and 19.3) antibodies and three comparator antibodies (Comp 1, 2, and 3) to monomeric Aβ, ADDLs and fibrillar Aβ. Comparative antibody 2 is known to be non-selective antibody for ADDLs. The background of this assay was determined by removing the capture antibody from the ELISA (no mAb). Error bars represent standard error of the mean.

This invention provides a kit and method for reliably and sensitively detecting Aβ oligomers in a biological sample, such as the CSF of a patient for use as both a pharmacodynamic and target engagement measure of Aβ oligomers. The kit and method of the invention can differentiate AD from non-AD patients and stratify AD disease state based on elevated levels of Aβ oligomers in, for example the CNS of the AD patients, similar to uses previously reported for a tau/Abeta42 CSF ratio (De Meyer, et al. (2010) *Arch. Neurol.* 67:949-56). Moreover, an Aβ oligomer assay, detecting the most neurotoxic species, may correlate better and be a more dynamic measure of changes in cognitive performance, as compared to the poor correlation observed for levels of Aβ monomer. It has now been demonstrated that a peripherally administered anti-Aβ oligomer antibody can penetrate the blood-brain-barrier and bind Aβ oligomers and, when used in combination with the method herein, can provide a surrogate end-point assay for the assessment of AD therapeutics.

For the purposes of this invention, the term "Aβ oligomers" refers to multimer species of Aβ monomer that result from self-association of monomeric species. Aβ oligomers are predominantly multimers of Aβ1-42, although Aβ oligomers of Aβ1-40 have been reported. Aβ oligomers may include a dynamic range of dimers, trimers, tetramers and higher-order species following aggregation of synthetic Aβ monomers in vitro or following isolation/extraction of Aβ species from human brain or body fluids. ADDLs are one species of Aβ oligomers.

The term "ADDLs" or "amyloid β-derived diffusible ligands" or "amyloid β-derived dementing ligands" as used herein refers to a neurotoxic, soluble, globular, non-fibrillar oligomeric structure containing two or more Aβ protein monomers. Higher order oligomeric structures can be obtained not only from Aβ1-42, but also from any Aβ protein capable of stably forming the soluble non-fibrillar Aβ oligomeric structures, such as Aβ1-43 or Aβ1-40. See U.S. Pat. No. 6,218,506 and WO 01/10900.

The term "Aβ fibrils" or "fibrils" or "fibrillar amyloid" as used herein refers to insoluble species of Aβ that are detected in human and transgenic mouse brain tissue because of their birefringence with dyes such as thioflavin S. Aβ species that form fiber-like structures comprised of Aβ monomers include β-pleated sheets. These species are believed to be immediate precursors to the extracellular amyloid plaque structures found in AD brain.

The term "Aβ1-40 monomer" or "Aβ1-42 monomer" as used herein refers to the direct product of the enzymatic cleavage, i.e., aspartic protease activity, by β-secretase and γ-secretase on the amyloid protein precursor (APP) in a cell-free or cellular environment. Cleavage of APP by β-secretase generates the Aβ species beginning at Asp 1 (numbering as to Aβ peptide sequence after cleavage), while γ-secretase liberate the C-terminus of Aβ, predominantly either at residues 40 or 42.

A highly sensitive assay has now been developed to detect and measure the levels of Aβ oligomers in a biological sample, e.g., a fluid sample, preferably CSF. The kit and method of the invention use two anti-Aβ oligomer-selective antibodies as capture and detection antibodies in a competitive binding assay, such as a sandwich ELISA. The term "capture antibody" or "Aβ oligomer capture antibody" or "anti-human IgG2 capture antibody" as used herein refers to an antibody that is used as the capture antibody in the assays herein. The capture antibody as used herein binds to an Aβ oligomer or Aβ oligomer/antibody complex that are being measured and/or detected in a sample.

According to the kit and method, the capture antibody is characterized as recognizing an N-terminal linear epitope of amyloid beta 1-42 peptide, having a higher affinity for amyloid beta 1-42 oligomers than for amyloid beta 1-42 monomer, amyloid beta 1-40 monomer, plaques and amyloid beta fibrils, and exhibiting exhibits less than a 10-fold decrease in $EC_{50}$ when stored at 40° C. for month; and the detection antibody is characterized as recognizing an N-terminal linear epitope of amyloid beta 1-42 peptide.

As is known in the art, a linear epitope is an epitope, wherein an amino acid primary sequence includes the epitope recognized. A linear epitope typically includes at least 3, and more usually, at least 5, for example, about 8 to about 10 amino acids in a unique sequence. In particular embodiments of this invention, the capture and detection antibody both recognize a linear epitope at the N-terminus of the Aβ1-42 peptide and this linear epitope may be the same or different. In certain embodiments, the, or each, linear epitope is located within residues 1-20 of Aβ1-42 peptide, or in the N-terminal 10, 11, 12, 15 or 20 amino acid residues of amyloid β1-42. In particular embodiments, an antibody of the invention specifically binds to a linear epitope within residues 1-5, 1-8, 1-10, 1-20, 3-8, or 3-10 of amyloid β1-42 and this linear epitope may be the same or different for each of the capture and detection antibody.

The linear epitope of an antibody can be readily mapped by generating a set of overlapping, five-ten amino acid peptides of Aβ1-42, and determining binding of the antibody the set of peptides in a competitive binding assay, such as an ELISA assay. Using such an assay the core linear epitope of various commercial antibodies have been determined. Based upon the analysis presented in U.S. Pat. No. 7,780,963 and Horikoshi, et al. (2004) supra, the linear epitopes of antibodies of use in this invention are presented in Table 1.

TABLE 1

| Antibody | Core Epitope | Epitope Sequence within Aβ1-42 DAEFRHDSGYEVHHQKLVFFAEDVGSNKGAIIGLMVGGVVIA | SEQ ID NO: 7 |
|---|---|---|---|
| 6E10 | 5-11 | RHDSGYE | 8 |
| BAM-10 | 3-8 | EFRHDS | 9 |

TABLE 1-continued

| Antibody | Core Epitope | Epitope Sequence within Aβ1-42 DAEFRHDSGYEVHHQKLVFFAEDVGSNKGAIIGLMVGGVVIA | SEQ ID NO: 7 |
|---|---|---|---|
| 4G8 | xx-21 | EVHHQKLVFFA | 10 |
| WO-2 | 3-8 | EFRHDS | 9 |
| 26D6 | 3-8 | EFRHDS | 9 |
| 2A10[a] | 3-8 | EFRHDS | 9 |
| 2B4[b] | 3-8 | EFRHDS | 9 |
| 4C2[a] | 3-8 | EFRHDS | 9 |
| 4E2[a] | 3-8 | EFRHDS | 9 |
| 2H4[c] | 1-8 | DAEFRHDS | 11 |
| 20C2[a] | 3-8 | EFRHDS | 9 |
| 2D6[a] | 3-8 | EFRHDS | 9 |
| 5F10[c] | 3-8 | EFRHDS | 9 |
| 1F4[a] | * | | |
| 1F6[a] | * | | |
| 2E12[a] | 3-10 | EFRHDSGY | 12 |
| 3B3[a] | * | | |
| 82E1 | 1-5 | DAEFR | 13 |

Core epitope position is with respect to Aβ1-42.
[a]IgG1,
[b]IgG2b,
[c]IgG2a.
*Epitopes were estimated to be located at the N-terminus of Aβ1-42, as they could bind to Aβ1-20 peptide.

The 19.3 antibody was evaluated as a potential capture reagent for Aβ oligomers in combination with three different antibodies as detection antibodies 19.3, 7305 (i.e., 20C2, U.S. Pat. No. 7,780,963, which is incorporated herein by reference in its entirety), and 82E1, following their biotinylation, in a sandwich ELISA format. Biotinylated 19.3 was examined as a detection antibody and paired with 19.3 as the capture antibody, in a test of overlapping epitopes. The presence of overlapping epitopes would be indicative of an Aβ construct with multiple epitopes, which suggests the presence of a dimer or higher order Aβ oligomers. The 19.3×19.3 overlapping epitope ELISA had a limit of detection (LoD) for Aβ oligomers of 98 pg/mL. Sandwich ELISAs for the antibody pair 19.3 and 82E1 had a LoD of 1.3 pg/mL and a lower limit of reliable quantification (LLoRQ) of 4.2 pg/mL for Aβ oligomers and the ratio of signal from Aβ oligomers/Aβ monomer was approximately 1000:1, showing that the assay was 1000 fold more selective for Aβ oligomers over Aβ40 monomer. Therefore, while both the capture and detection antibodies of the kit and method of this invention both recognize the N-terminal portion of Aβ1-42, in certain embodiments, the epitope of the capture and detection antibody do not overlap or overlap by less than 3, 2, or 1 amino acid residue.

To provide specificity for oligomers of Aβ, particular embodiments of this invention embrace the use of a capture antibody that recognizes a linear epitope and a conformational epitope. Such an antibody is described herein as being selective or specific for Aβ oligomers. As is known in the art, a conformational epitope is an epitope wherein the primary sequence of the amino acids comprising the epitope is not the sole defining component of the epitope recognized. Typically a conformational epitope encompasses an increased number of amino acids relative to a linear epitope. With regard to recognition of conformational epitopes, the antibody recognizes a three-dimensional structure of the peptide or protein. For example, when a protein molecule folds to form a three-dimensional structure, certain amino acids and/or the polypeptide backbone forming the conformational epitope become juxtaposed enabling the antibody to recognize the epitope. Methods of determining conformation of epitopes include but are not limited to, for example, x-ray crystallography, two-dimensional nuclear magnetic resonance spectroscopy and site-directed spin labeling and electron paramagnetic resonance spectroscopy. See, for example, Epitope Mapping Protocols in Methods in Molecular Biology (1996) Vol. 66, Morris (Ed.).

Preferably, a capture antibody that is selective for Aβ oligomer has a higher affinity for Aβ1-42 oligomers or ADDLs than for Aβ1-42 monomer, Aβ1-40 monomer, plaques and/or amyloid beta fibrils. As demonstrated herein, selectivity can be assessed using a variety of methods including, but not limited to competitive binding assays such as one-sided ELISA, sandwich ELISA or competitive ELISA assays. Using such assays (Example 15 and FIG. 1), a number of antibodies, e.g., h3B3, 14.2, 7.2, 11.4, 13.1, 17.1, 19.3, 20C2, 2A10, 2B4, 2D6, 5F10, 4E2, 4C2, and W0-2, were found to selectively bind oligomers over amyloid beta 1-40 monomer and fibrils. Based upon this analysis, an antibody is defined as being specific for Aβ oligomers if it exhibits at least a 2-fold, 3-fold, 4-fold, 5-fold higher affinity for Aβ oligomers compared to one or more of Aβ1-42 monomer, Aβ1-40 monomer, plaques or amyloid beta fibrils when assessed in a conventional assay, e.g., BIACORE, KINEXA, or one-sided ELISA. In particular embodiments, the affinity of the capture antibody for Aβ1-42 oligomers compared to Aβ1'-40 monomers in a competitive binding assay is at least 500:1. In other embodiments, the affinity of the capture antibody for amyloid beta 1-42 oligomers compared to amyloid beta 1-42 monomers in a sandwich ELISA assay is at least 500:1, at least 600:1, at least 700:1, at least 800:1, at least 900:1 or more preferably at least 1000:1.

In particular embodiments of this invention, variants of antibody h3B3 (i.e., 14.2, 7.2, 11.4, 13.1, 17.1, 19.3), or variants of antibody 19.3 (i.e., 19.3 N33S, 19.3 N33T, 19.3 N33A, 19.3 N33E, 19.3 N33D, 19.3 N33S-N35Q, 19.3 N33S-N35S, 19.3 N33S-N35T, 19.3 N33S-N35A, 19.3 N58Q, 19.3 N58S, 19.3 N58T, 19.3N35A) are used as the capture antibody in the kit and method of this invention. Accordingly, in some embodiments, a capture antibody of the kit and method of the invention has a light chain variable region with a CDR1 having the sequence Arg-Ser-Ser-Gln-Ser-Ile-Val-His-Ser-Xaa$_1$-Gly-Xaa$_2$-Thr-Tyr-Leu-Glu (SEQ ID NO:1), wherein Xaa$_1$ is Asn, Ser, Thr, Ala, Asp or Glu and Xaa$_2$ is Asn, His, Gln, Ser, Thr, Ala, or Asp, a CDR2 having the sequence Lys-Ala-Ser-Xaa$_1$-Arg-Phe-Ser (SEQ ID NO:2), wherein Xaa$_1$ is Asn, Gly, Ser, Thr, or Ala, and a CDR3 having the sequence Phe-Gln-Gly-Ser-Xaa$_1$-Xaa$_2$-Xaa$_3$-Xaa$_4$-Xaa$_5$ (SEQ ID NO:3), wherein Xaa$_1$ is Arg, Lys or Tyr, Xaa$_2$ is Val, Ala, or Leu, Xaa$_3$ is Pro, His, or Gly, Xaa$_4$ is Ala, Pro, or Val, and Xaa$_5$ is Ser, Gly, or Phe; and a heavy chain variable region with a CDR1 having the sequence Gly-Phe-Thr-Phe-Ser-Ser-Phe-Gly-Met-His (SEQ ID NO:4), a CDR2 having the sequence Tyr-Ile-Ser-Arg-Gly-Ser-Ser-Thr-Ile-Tyr-Tyr-Ala-Asp-Thr-Val-Lys-Gly (SEQ ID NO:5), and a CDR3 having the sequence Gly-Ile-Thr-Thr-Ala-Leu-Asp-Tyr (SEQ ID NO:6). Accordingly, in some embodiments, a capture antibody of the kit and method of the invention has a light chain variable region with a CDR1 having the sequence Arg-Ser-Ser-Gln-Ser-Ile-Val-His-Ser-Xaa$_1$-Gly-Xaa$_2$-Thr-Tyr-Leu-Glu (SEQ ID NO:1), wherein Xaa$_1$ is Thr, Ala, Asp or Glu and Xaa$_2$ is Asn, His, Gln, Ser, Thr, Ala, or Asp or wherein Xaa$_1$ is Asn, Ser, Thr, Ala, Asp or Glu and Xaa$_2$ is Thr, a CDR2 having the sequence Lys-Ala-Ser-Xaa$_1$-Arg-Phe-Ser (SEQ ID NO:2), wherein Xaa$_1$ is Thr, and a CDR3 having the sequence Phe-Gln-Gly-Ser-Xaa$_1$-Xaa$_2$-Xaa$_3$-Xaa$_4$-Xaa$_5$ (SEQ ID NO:3), wherein Xaa$_1$ is Arg, Lys or Tyr, Xaa$_2$ is Val, Ala, or Leu, Xaa$_3$ is Pro, His, or Gly, Xaa$_4$ is Ala, Pro, or Val, and Xaa$_5$ is Ser, Gly, or Phe; and a heavy chain variable region with a CDR1 having the sequence Gly-Phe-Thr-Phe-Ser-Ser-Phe-Gly-Met-His (SEQ ID NO:4), a CDR2 having the sequence Tyr-Ile-Ser-Arg-Gly-Ser-Ser-Thr-Ile-Tyr-Tyr-Ala-Asp-Thr-Val-Lys-Gly (SEQ ID NO:5), and a CDR3 having the sequence Gly-Ile-Thr-Thr-Ala-Leu-Asp-Tyr (SEQ ID NO:6) and such a capture antibody also forms part of the present invention.

In some embodiments, the capture antibody of the kit and method of the invention is a variant of antibody h3B3 (i.e., 14.2, 7.2, 11.4, 13.1, 17.1, 19.3). In accordance with this embodiment, the capture antibody has a light chain variable region with a CDR1 having the sequence Arg-Ser-Ser-Gln-Ser-Ile-Val-His-Ser-Asn-Gly-Asn-Thr-Tyr-Leu-Glu (SEQ ID NO:14), a CDR2 having the sequence Lys-Ala-Ser-Asn-Arg-Phe-Ser (SEQ ID NO:15), and a CDR3 of SEQ ID NO:3; and a heavy chain variable region with a CDR1 of SEQ ID NO:4, a CDR2 of SEQ ID NO:5, and a CDR3 of SEQ ID NO:6.

In other embodiments, the capture antibody of the kit and method of the invention is a variant of antibody 19.3, wherein the CDR1 of the light chain variable region has been mutated (i.e., 19.3 N33S, 19.3 N33T, 19.3 N33A, 19.3 N33E, 19.3 N33D, 19.3 N33S-N35Q, 19.3 N33S-N35S, 19.3 N33S-N35T, 19.3 N33S-N35A). In accordance with this embodiment, the capture antibody has a light chain variable region with a CDR1 of SEQ ID NO:1, a CDR2 of SEQ ID NO:15, and a CDR3 having the sequence Phe-Gln-Gly-Ser-Arg-Leu-Gly-Pro-Ser (SEQ ID NO:16); and a heavy chain variable region with a CDR1 of SEQ ID NO:4, a CDR2 of SEQ ID NO:5, and a CDR3 of SEQ ID NO:6.

In still other embodiments, the capture antibody of the kit and method of the invention is a variant of antibody 19.3, wherein the CDR2 of the light chain variable region has been mutated (i.e., 19.3 N58Q, 19.3 N58S, 19.3 N58T, 19.3N35A). In accordance with this embodiment, the capture antibody has a light chain variable region with a CDR1 of SEQ ID NO:14, a CDR2 of SEQ ID NO:2, a CDR3 of SEQ ID NO:16; and a heavy chain variable region with a CDR1 of SEQ ID NO:4, a CDR2 of SEQ ID NO:5, and a CDR3 of SEQ ID NO:6.

In certain embodiments, the CDR1 of the light chain variable region of the capture antibody has the sequence Arg-Ser-Ser-Gln-Ser-Ile-Val-His-Ser-Xaa$_1$-Gly-Xaa$_2$-Thr-Tyr-Leu-Glu (SEQ ID NO:1), wherein Xaa$_1$ is Thr, Ala, Asp or Glu and Xaa$_2$ is Thr. In other embodiments, the CDR2 of the light chain variable region of the capture antibody has the sequence Lys-Ala-Ser-Xaa$_1$-Arg-Phe-Ser (SEQ ID NO:2), wherein Xaa$_1$ is Thr.

To facilitate production and enhance storage and use of the capture antibody in the kit and method of this invention, certain embodiments include the use of a capture antibody that exhibits less than a 10-fold decrease in $EC_{50}$, in an ELISA-based assay with Aβ oligomers, when stored at 40° C. for 1 month. More preferably, the capture antibody exhibits less than a 6-fold, 5-fold, 4-fold, 3-fold, or 2-fold decrease in $EC_{50}$ when stored at 40° C. for 1 month. Antibody stability can be assessed as described in the Examples herein. Antibodies having such stability at elevated temperatures are provided in Examples 7 and 9.

While the detection antibody recognizes a linear epitope located in the N-terminus of Aβ1-42, said antibody may or may not also bind a conformational epitope. In this respect, there are number of antibodies of use as the detection antibody in the kit and method of this invention. As provided in Table 1, any one of antibodies 6E10, BAM-10, W0-2, 26D6, 2A10, 2B4, 4C2, 4E2, 2H4, 20C2, 2D6, 5F10, 1F4, 1F6, 2E12, 3B3 or 82E1 recognize a linear epitope located in the N-terminus of Aβ1-42 and is therefore of use in the kit and method of the invention. In certain embodiments, the detection antibody binds a 5 to 10 amino acid residue N-terminal epitope of Aβ1-42 having the sequence DAEFR (SEQ ID NO:13). In particular embodiments, the detection antibody is 82E1.

To facilitate detection of a capture antibody/Aβ oligomer/detection antibody complex, certain embodiments include the use of a labeled detection antibody. A variety of labels are well-known in the art and can be adapted to the practice of this invention. For example, fluorescent labels, luminescent labels and light-scattering labels (e.g., colloidal gold particles) have been described. See, e.g., Csaki et al. (2002) *Expert. Rev. Mol. Diagn.* 2:187-93.

Fluorescent labels of use in this invention include, but not limited to, hydrophobic fluorophores (e.g., phycoerythrin, rhodamine, ALEXA FLUOR 488, ALEXA FLUOR 546 and fluorescein), green fluorescent protein (GFP) and variants thereof (e.g., cyan fluorescent protein and yellow fluorescent protein), and quantum dots. See e.g., Haughland (2003) *Handbook of Fluorescent Probes and Research Products*, Ninth Edition or Web Edition, from Molecular Probes, Inc., or *The Handbook: A Guide to Fluorescent Probes and Labeling Technologies*, Tenth Edition or Web Edition (2006) from Invitrogen for descriptions of fluorophores emitting at various different wavelengths. For use of quantum dots as labels for biomolecules, see e.g., Dubertret, et al. (2002) *Science* 298:1759; *Nature Biotech.* (2003) 21:41-51. In particular embodiments, the label is a hydrophobic fluorophores such as an ALEXA FLUOR.

Labels can be introduced onto the detection antibody by techniques established in the art. For example, kits for fluorescently labeling antibodies with various fluorophores are available from Invitrogen Corp. Similarly, signals from the labels (e.g., absorption by and/or fluorescent emission from a fluorescent label) can be detected by the techniques exemplified herein (i.e., ENVISION or ERENNA system, wherein the fluorescent tagged detecting antibody is uncoupled from the sandwich ELISA complex and subsequently detected) or by essentially any method known in the art. For example, multicolor detection, detection of FRET, fluorescence polarization, and the like, are well-known in the art. For example, flow cytometers are widely available, e.g., from Becton-Dickinson and Beckman Coulter and LUMINEX 100 and LUMINEX HTS systems are available from Luminex Corporation.

To enhance the sensitivity of the kit and method of this invention for Aβ oligomers, one embodiment of this invention includes the use of a means or substrate for concentrating an antibody-antigen complex. As demonstrated herein, the performance of two antibody pairs was assessed in a paramagnetic microparticle detection system, specifically the ERENNA system (SINGULEX, Almeda, Calif.), employing detection of a fluorescent tagged detecting antibody that is uncoupled from the sandwich ELISA complex. Performance of a 19.3×82E1 sandwich ELISA was improved such that the 19.3×82E1 antibody pair enabled detection of Aβ oligomer signals in AD CSF samples at higher levels compared to either age-matched or younger control samples. More specifically, the assay LoD improved approximately thirty-fold, to 0.04 pg/mL, while the LoRQ improved ten-fold, to 0.42 pg/mL. Similarly, the Aβ oligomer/Aβ monomer ratio was also improved, to 5000:1. Therefore, a means or substrate for concentrating an antibody-antigen complex can be used to increase the sensitivity of the kit and method of this invention.

Substrates for concentrating antigen-antibody complexes are known in the art and include, but are not limited to solid surfaces (e.g., beads), fluorescent polymeric beads, magnetic beads, which can be bonded or attached to the capture antibody.

Solid surfaces, such as beads, can be bound to the capture antibody, such that the capture antibody/Aβ oligomer/detection antibody complex can be concentrated by centrifugation or filtration. Fluorescent beads can be prepared, for example, by embedding or covalently coupling a fluorescent dye onto a polymeric particle and attaching the particle to the capture antibody. The fluorescent microparticles can be analyzed manually or by other methods known in the art but preferably using an automated technique, e.g., flow cytometry, such as disclosed in U.S. Pat. No. 4,665,024. The versatility of the fluorescent particles can be further enhanced by the incorporation of multiple fluorescent materials in a single particle. Magnetic particles, including, paramagnetic and superparamagnetic can alternatively be used to concentrate antibody-antigen complexes via a magnetic field. Such particles are known in the art and, in addition to their magnetic properties (i.e. magnetic, paramagnetic, and superparamagnetic), can be classified, for example, into three broad categories based on their relative descending size: magnetic particulate labels, colloidal magnetic labels, and molecular magnetic labels, see for example U.S. Pat. No. 6,412,359. In certain embodiments, the capture antibody is bound to a magnetic microparticle as described in the method described herein.

Using the kit and method of this invention, it has been demonstrated that the level of detection of amyloid beta 1-42 oligomers is less than 5 pg/mL. Indeed, using two anti-Aβ oligomer antibodies, 19.3 and 82E1, along with paramagnetic micro-particle detection, in a sandwich ELISA assay, it has now been shown that Aβ oligomers can be detected in a biological sample to a limit of detection of 40 fg/mL. Accordingly, in some embodiments of this invention, the limit of detection of the kit and method of the invention is less than 5 pg/mL, less than 3 pg/mL, less than 1 pg/mL, less than 500 fg/mL, or less than 100 fg/mL. In certain embodiments, the limit of detection of the kit and method of the invention is in the range of 40 fg/mL and 5 pg/mL.

The term "limit of detection" of "LoD," as used herein, refers to the sensitivity of the assays at the lowest concentration that can be detected above a sample which is identical except for the absence of the Aβ oligomers. The signal in the absence of Aβ oligomers is defined as the "Background." As used herein, the LoD for Aβ oligomers was defined as ≥3 standard deviations above the mean of the background. The "lower limit of reliable quantification" or "LLoRQ," as used herein, refers to the sensitivity of the assay in combination with the coefficient of variability to indicate the lowest concentration that can be reliably and reproducibly differentiated from background. This limit typically defines the practical working range of the assay at the low end of sensitivity and is the concentration that delivers a coefficient of variability of ≤20% across ≥ three measured values.

While Aβ oligomers have been found in biological samples, particularly in CSF (Georganopoulou, at al. (2005) supra; Klyubin, et al. (2008) supra), the limits associated with known detection methods (including both sensitivity and selectivity) have not enabled this level of reliable detection, let alone, quantification of Aβ oligomers for use to classify the disease state of the patient or for the development of AD therapeutics. In contrast, using the method of this invention, highly significant elevations in Aβ oligomers were demonstrated in clinically confirmed AD samples as compared to either young or age-matched controls. These same samples were used to measure levels of Aβ1-42 and Aβ1-40 monomer and confirmed that in the AD samples Aβ1-42 monomer was significantly reduced as compared to the controls, while the Aβ1-40 monomer levels were unchanged. The Aβ oligomer sandwich ELISA assay demonstrated significant correlations between Aβ oligomer concentration and performance on a cognitive test widely used to measure AD severity, known as the Mini-Mental State Exam (MMSE); the higher the cognitive score (up to a value of 30, which is cognitively normal) the lower the level of Aβ oligomer in the CSF. Accordingly, in some embodiments of this invention, the method and kit are of use in confirming a diagnosis or diagnosing AD or AD severity. In addition, the kit and method of this invention can be used to identify patients at an early stage of disease (i.e., a prognostic assay).

Therefore, this invention also provides a method for detecting oligomers of Aβ. In accordance with this method, a biological sample having oligomers of Aβ is obtained from an animal, preferably a human; the biological sample is contacted with a capture antibody, as described herein, under conditions sufficient to form a capture antibody/oligomer of Aβ complex; the capture antibody/oligomer of Aβ complex is then detected using a detection antibody, as described herein. In other embodiments of this method, a biological sample from an animal, preferably a human, is contacted with a capture antibody, as described herein, under conditions sufficient to form a capture antibody/oligomer of Aβ complex; the capture antibody/oligomer of Aβ complex is then detected using a detection antibody, as described herein. The term "biological sample" or "fluid sample," as used herein, refers to any type of fluid, as compared to a tissue, or a vertebrate. Typical examples that may be used in the assays herein are blood, urine, tears, saliva, and cerebrospinal fluid, which is used in one embodiment of the invention. All other kinds of body fluids may also be used if Aβ oligomers are present. However, in particular embodiments, the biological sample is CSF.

This method is a sensitive and selective competitive binding assay, such as a sandwich ELISA assay, which detects and quantifies endogenous Aβ oligomers in biological samples such as CSF samples from both AD and human control individuals. While Alzheimer's disease or AD is particularly described herein as one condition that can be diagnosed using the kit and method of this invention, the spectrum of dementias or cognitive impairment resulting from neuronal degradation associated with the formation of Aβ oligomers or formation or deposition of Aβ plaques or neurofibrillar tangles includes, but not limited to, Down's Syndrome, Lewy body dementia, Parkinson's disease, preclinical Alzheimer's disease, mild cognitive impairment due to Alzheimer's disease, early onset Alzheimer's disease (EOD), familial Alzheimer's disease (FAD), thru the advance cognitive impairment of dementia due to Alzheimer's disease (Jack, et al. (2011) *Alzheimer's Dement.* 7(3):257-262), and diseases associated with the presence of the ApoE4 allele. Therefore, the kit and method can be used in the diagnosis of any one of these diseases or conditions.

The invention is described in greater detail by the following non-limiting examples.

Example 1

Aβ Preparations

Aβ1-40 and Aβ1-42 (amyloid β peptide 1-40, amyloid β peptide1-42) were obtained from the American Peptide Co. (Sunnyvale, Calif.).

Monomer Preparation.

To generate monomer preparations, Aβ1-40 or Aβ1-42 was dissolved in 1,1,1,3,3,3 hexafluoro-2-propanol (HFIP; Sigma-Aldrich, St. Louis, Mo.) to eliminate any pre-existing secondary structure that could act as a "seeds" for aggregation. The HFIP was removed by evaporation to form an Aβ1-40 or Aβ1-42 peptide film. Room temperature Aβ1-40 or Aβ1-42 peptide film was dissolved in 2 mL of 25 mM borate buffer (pH 8.5) per mg of peptide, divided into aliquots, and frozen at −70° C. until used.

ADDL Preparation.

The Aβ42 peptide film (1 mg Aβ42 dried down from 100% HFIP solvent) was dissolved in 44 µL of DMSO, to which 1956 µl of cold F12 media (GIBCO®, Invitrogen, Carlsbad, Calif.) was added with gentle mixing. The mixture was incubated at room temperature for 18 to 24 hours. Samples were centrifuged at 14,200 g for 10 minutes at room temperature. Supernatant was transferred to a fresh tube and was filtered through 0.5 ml column YM-50 filter tube (Millipore, Bedford Mass.; 0.5 ml) via centrifugation at 4,000 rpm for 15 minutes at 4° C. The retentate was collected by reversing the filter insert, replaced into a new collection tube, and centrifuged at 4,000 rpm for 5 minutes at 4° C. Protein concentration was measured pre-filtration by Bradford Assay (BioRad, Her-cules, Calif.) and reported as µM (calculated based on Aβ monomer molecular weight (MW 4513)). All samples were stored at −80° C. until used.

Biotinylated ADDLs (bADDLs) Preparation.

bADDLs were prepared using the same method as described for ADDLs, with N-terminal biotinylated Aβ 1-42 peptide (American Peptide, Sunnyvale, Calif.) as the starting material.

Fibril Preparation.

The fibril preparations were made by adding 2 mL of 10 mM hydrochloric acid per mg of Aβ1-42 peptide film. The solution was mixed on a vortex mixer at the lowest possible speed for five to ten minutes and the resulting preparation was stored at 37° C. for 18 to 24 hours before use.

Example 2

Preparation of Affinity-Matured 3B3 Antibodies

Panning Humanized Antibody Library.

An affinity mature library of a humanized anti-ADDL antibody, h3B3, (See U.S. Pat. Nos. 7,811,563 and 7,780,963) was constructed in which part of the light chain CDR3 amino acid sequence was subjected to random mutagenesis. To cover the entire CDR3 region, two sub-libraries were built. One library was composed of the parental heavy chain variable region and mutated amino acids in the left half of the light chain CDR3 and the other in the right half of the light chain CDR3. A similar strategy was used for heavy chain CDRs random mutagenesis with three sub-libraries.

Humanized 3B3 was subjected to affinity maturation using methods known in the art. The h3B3 variable regions were cloned in a Fab display vector (pFab3D). In this vector, the variable regions for heavy and light chains were inserted in-frame to match the CH1 domain of the constant region and the kappa constant region, respectively. In Fab3D, myc epitope and six consecutive histidine amino acid residues follow the CH1 sequence, which is then linked to the phage pIII protein for display. All positions in the heavy and light chain CDR3s were randomly mutagenized using degenerate oligonucleotide sequences incorporated into the PCR primers. To accommodate the physical size, the sub-libraries were constructed with each focusing on 5-6 amino acid residues. The vector DNA of h3B3 was used as template DNA to amplify both heavy and light chains with the mutated PCR primers (Table 2). After PCR amplification, the synthesized DNA fragments were separated on a 1.3% agarose gel, the primers removed and the variable fragments digested with restriction enzymes: BsiWI and XbaI cloning sites for light chain variable cloning, XhoI and ApaI for heavy chain variable cloning.

TABLE 2

| 3B3 Affinity Maturation Library | Primer | Primer Sequence | SEQ ID NO: |
|---|---|---|---|
| Light Chain Libraries | Forward | tatggcttctagagatgtggtgatg | 17 |
| | Reverse | tgcagccaccgtacgcttgatctcc agcttggtgccctggccaaaggtgg ggggcacmnnmnnmnnmnnmnnngca gtagtag | 18 |
| | | tgcagccaccgtacgcttgatctcc agcttggtgccctggccaaamnnmn nmnnmnnmnnngctgccctgg | 19 |

TABLE 2-continued

| 3B3 Affinity Maturation Library | Primer | Primer Sequence | SEQ ID NO: |
|---|---|---|---|
| Heavy Chain Libraries | Forward | aggcggccctcgaggaggtgcagc | 20 |
| | Reverse | agaccgatgggcccttggtggaggc gctggacacggtcaccagggtgccc tggccccamnnmnnmnnmnnmnngg tgatgccc | 21 |
| | | agaccgatgggcccttggtggaggc gctggacacggtcaccagggtgccc tggccccagtagtccagmnnmnnmn nmnnmnnccgggcacag | 22 |

M = A/C, N = A/C/G/T.

To construct an affinity maturation library in pFab3D phage display vector, pFab3D-3B3 DNA was digested with the same pair of the restriction enzymes, purified and the PCR fragments for heavy or light chain variables ligated with T4 ligase (Invitrogen, Carlsbad, Calif.) overnight at 16° C. The ligation products were then transfected into *E. coli* TG1 electroporation-competent cells (Stratagene, Agilent Technologies, Santa Clara, Calif.) and aliquots of the bacterial culture plated on LB agar-carbenicillin (50 μg/mL) plates to titer library size. The remaining cultures were either plated on a large plate with carbenicillin and incubated at 30° C. overnight for *E. coli* library stock or infected with helper phage M13K07 (Invitrogen, Carlsbad, Calif.; $10^{11}$ pfu/mL) by incubating at room temperature and 37° C. for ten minutes. Subsequently, 2TY medium with carbenicillin (50 μg/mL) was added and the culture was incubated at 37° C. for one hour with shaking. Kanamycin (70 μg/ml) was then added and the cultures grown overnight at 30° C. with shaking. The phage culture supernatant was titered and concentrated by precipitation with 20% (v/v) PEG (polyethylene glycol)/NaCl, resuspended in PBS, sterilized with a 0.22 μm filter, and aliquots made for phage library panning.

The phage library panning was then conducted as summarized in Table 3.

TABLE 3

| | Panning Rounds | | | |
|---|---|---|---|---|
| | Round 1 | Round 2 | Round 3 | Round 4 |
| Antigen concentration | 180 nM | 60 nM | 20 nM | 10 nM |

Input phage from the Fab display phage libraries (100 μl, about $10^{11-12}$ pfu) were blocked with 900 μL of blocking solution (3% non-fat dry milk in PBS) to reduce nonspecific binding to the phage surface. Streptavidin-coated beads were prepared by collecting 200 μL of the bead suspension in a magnetic separator and removing supernatants. The beads were then suspended in 1 mL of blocking solution and put on a rotary mixer for 30 minutes. To remove non-specific streptavidin binding phage, the blocked phage library was mixed with the blocked streptavidin-coated beads and placed on a rotary mixer for thirty minutes. Phage suspensions from the de-selection process were transferred to a new tube and 200 μL of antigen, 10% bADDL, was added and incubated for two hours for antibody and antigen binding. After the incubation, the mixture was added into the blocked streptavidin-coated beads and incubated on a rotary mixer for one hour to capture the antibody/antigen complex on streptavidin beads. The beads with captured 10% bADDL/phage complexes were washed five times with PBS/0.05% TWEEN 20 and then twice with PBS alone. The bound phages were eluted from the bADDL with 200 μL of 100 mM TEA and incubated for twenty minutes. The eluted phage were then transferred to a 50 mL tube, neutralized with 100 μL of 1 M Tris-HCl, pH 7.5, and added to 10 mL of *E. coli* TG1 cells with an OD600 nm between 0.6-0.8. After incubation at 37° C. with shaking for one hour, culture aliquots were plated on LB agar-carbenicillin (50 μg/mL) plates to titer the output phage number, and the remaining bacteria centrifuged and suspended with 500 μl 2xYT medium (Teknova, Hollister, Calif.), plated on bioassay YT agar plates (Teknova, Hollister, Calif.) containing 100 μg/ml ampicillin and 1% glucose. The bioassay plates were grown overnight at 30° C.

After each round of panning, single colonies were randomly picked to produce phage in 96-well plates. The procedure for phage preparation in 96-well plates was similar to that described above except no phage precipitation step was used. Culture plates containing colonies growing in 120 μL of 2xYT medium (16 g BACTO-tryptone, 10 g BACTO-yeast extract, 5 g NaCl (all BD Biosciences, Franklin Lakes, N.J.), ddH$_2$O to 1 L) with 100 μg/ml ampicillin and 0.1% glucose were incubated overnight in a HIGRO shaker (Genomic Solutions, Ann Arbor, Mich.) at 30° C. with shaking at 450 rpm. The phage supernatants (about 100 μL) were directly used for analysis in the ADDL binding ELISA. Binding of phage to ADDLs was detected with an anti-M13-antibody conjugated to horseradish peroxidase (HRP) (Amersham Bioscience, GE Healthcare, Waukesha, Wis.).

Example 3

Selection of Affinity Matured 3B3 Antibodies

From the light chain affinity maturation effort, a panel of seven clones (11.4, 17.1, 14.2, 13.1, 19.3, 7.2 and 9.2) showed strong binding activities to ADDLs when compared with h3B3 in a phage/Fab ELISA. Table 4 shows the amino acid similarity for the clones selected from the light chain affinity maturation library relative to parental antibody, h3B3.

TABLE 4

| Antibody | 11.4 | 17.1 | 14.2 | 13.1 | 19.3 | 7.2 | 9.2 | h3B3-humanized LC |
|---|---|---|---|---|---|---|---|---|
| 11.4 | — | 98 | 98 | 96 | 96 | 96 | 97 | 97 |
| 17.1 | — | — | 98 | 96 | 97 | 96 | 97 | 97 |
| 14.2 | — | — | — | 96 | 97 | 98 | 98 | 98 |
| 13.1 | — | — | — | — | 97 | 97 | 97 | 96 |
| 19.3 | — | — | — | — | — | 96 | 97 | 96 |
| 7.2 | — | — | — | — | — | — | 98 | 96 |
| 9.2 | — | — | — | — | — | — | — | 97 |

Table 5 summarizes the amino acid sequences in CDR3 of the light chain (LC) of the selected clones compared to the CDR3 of the light chain for the parental antibody, h3B3.

TABLE 5

| Antibody | LC-CDR3 Sequence | SEQ ID NO: |
|---|---|---|
| h3B3 (parental) | FQGSHVPPT | 23 |
| 19.3 | FQGSRLGPS | 16 |
| 17.1 | FQGSRVPAS | 24 |
| 14.2 | FQGSRVPPG | 25 |

TABLE 5-continued

| Antibody | LC-CDR3 Sequence | SEQ ID NO: |
|---|---|---|
| 13.1 | FQGSKAHPS | 26 |
| 7.2 | FQGSYAPPG | 27 |
| 9.2 | FQGSRAPPF | 28 |
| 11.4 | FQGSRVPVR | 29 |

Table 6 provides the sequence of a portion (positions 21-117) of the light chain variable regions (LCVR) for the selected clones and the parental antibody, h3B3. CDR3 of each clone is shown in bold.

TABLE 6

| Ab | LCVR Sequence | SEQ ID NO: |
|---|---|---|
| h3B3 | PASISCRSSQSIVHSNGNTYLEWYLQKPGQSPQLLIYKASNRFSG VPDRFSGSGSGTDFTLKISRVEAEDVGVYYCFQGSHVPPTFGQGT KLEIK | 30 |
| 19.3 | PASISCRSSQSIVHSNGNTYLEWYLQKPGQSPQLLIYKASNRFSG VPDRFSGSGSGTDFTLKISRVEAEDVGVYYCFQGSRLGPSFGQGT KLEIK | 31 |
| 17.1 | PASISCRSSQSIVHSNGNTYLEWYLQKPGQSPQLLIYKASNRFSG VPDRFSGSGSGTDFTLKISRVEAEDVGVYYCFQGSRVPASFGQGT KLEIK | 32 |
| 14.2 | PASISCRSSQSIVHSNGNTYLEWYLQKPGQSPQLLIYKASNRFSG VPDRFSGSGSGTDFTLKISRVEAEDVGVYYCFQGSRVPPGFGQGT KLEIK | 33 |
| 13.1 | PASISCRSSQSIVHSNGNTYLEWYLQKPGQSPQLLIYKASNRFSG VPDRFSGSGSGTDFTLKISRVEAEDVGVYYCFQGSKAHPSFGQGT KLEIK | 34 |
| 7.2 | PASISCRSSQSIVHSNGNTYLEWYLQKPGQSPQLLIYKASNRFSG VPDRFSGSGSGTDFTLKISRVEAEDVGVYYCFQGSYAPPGFGQGT KLEIK | 35 |
| 9.2 | PASISCRSSQSIVHSNGNTYLEWYLQKPGQSPQLLIYKASNRFSG VPDRFSGSGSGTDFTLKISRVEAEDVGVYYCFQGSRAPPFFGQGT KLEIK | 36 |
| 11.4 | PASISCRSSQSIVHSNGNTYLEWYLQKPGQSPQLLIYKASNRFSG VPDRFSGSGSGTDFTLKISRVEAEDVGVYYCFQGSRVPVRFGQGT KLEIK | 37 |

Table 6

Example 4

IgG Conversion of Affinity Matured 3B3 Antibodies

The seven leading Fab clones (11.4, 17.1, 14.2, 13.1, 19.3, 7.2 and 9.2) were selected for IgG conversion. The converted IgGs were expressed using plasmid-based vectors. The expression vectors were built such that they contained all the necessary components except the variable regions. In the basic vectors, the expression of both light and heavy chains was driven by human CMV promoter and bovine growth hormone polyadenylation signal. For the seven clones selected for IgG conversion, the heavy chain variable region was in-frame fused with a human IgG2 heavy chain constant region (SEQ ID NOs:38 and 39), while the light chain variable region was in-frame fused with the kappa light chain constant region (SEQ ID NOs:40 and 41). The heavy (SEQ ID NOs:42 and 43) and light (SEQ ID NOs:44 and 45) chain leader sequences, which mediate the secretion of the antibodies into the culture media, were also in-frame fused with the variable regions accordingly. For the heavy chain expression vectors, the constant region could be selected from a different subclass isotype, e.g., IgG1 or IgG2. Between the leader sequence and the constant region, the intergenic sequences contain cloning sequences for seamless in-frame fusion of the incoming variable region with the leader sequence at its 5'-end and the constant region at its 3'-end using an IN-FUSION cloning strategy (Clontech, Mountain View, Calif.). The IN-FUSION Dry-Down PCR Cloning Kit (Clontech, Mountain View, Calif.) was used for PCR amplification of the variable regions. The dry-down cloning kit contained all the necessary components for PCR reaction. PCR primers and template DNAs were added. The expression vectors carry oriP from the EBV viral genome. The oriP/EBNA1 pair is often used to prolong the presence of the expression vector inside the transfected cells and widely used for the extension of the expression duration (Lindner, et al. (2007) *Plasmid* 58:1-12) for prolonged expression in 293EBNA cells, bacterial sequences for a kanamycin selection marker, and a replication origin in *E. coli*. When the variable regions were inserted, the IgGs were directly expressed in mammalian cells. All heavy chain variable regions herein were cloned into an IgG1 expression vector (pVl JNSA-BF-HCG1) and the light chain variable regions were cloned into a matching kappa or lambda expression vector (pVl JNSA-GS-FB-LCK).

Example 5

Affinity Matured 3B3 Antibody Cloning and Expression

The seven leading clones (11.4, 17.1, 14.2, 13.1, 19.3, 7.2 and 9.2) were produced as monoclonal antibodies and purified for further characterization. The cloning procedure for the resulting antibody expression vectors was as follows. The variable regions were PCR-amplified, wherein the PCR reactions were carried out in a volume of 25 µL containing high fidelity PCR master mix, template (1 µL), and forward and reverse primers (1 µL each). PCR conditions: 1 cycle of 94° C., 2 minutes; 25 cycles of 94° C., 1.5 minutes; 60° C., 1.5 minutes; 72° C., 1.5 minutes and 72° C., 7 minutes; 4° C. until removed. The PCR products were then digested with DpnI and purified with QIAQUICK plate kit (Qiagen, Venlo, The Netherlands). One hundred nanograms of the corresponding previously linearized heavy chain or light chain vectors was annealed to 10 ng of the PCR fragment with an IN-FUSION reaction (IN-FUSION Dry-Down Cloning Kit, Clontech, Mountain View, Calif.). The reaction mixture was transformed to XL2 Blue MRF' competent cells and plated overnight on agar plates containing 50 pg/mL kanamycin. Light chain constructs were digested with HindIII+NotI and heavy chain constructs were digested with AspI+HindIII to check structure by restriction analysis. The DNA sequences for all the clones were confirmed by sequence analysis.

Sequencing confirmed constructs of light chain and heavy chain DNA were transfected in 293 FREESTYLE cells (Invitrogen, Carlsbad, Calif.). The 293 FREESTYLE cells were transfected using 293 Transfectin (Invitrogen, Carlsbad, Calif.). EBNA monolayer cells were transfected using polyethylenimine-based transfection reagents. Transfected cells were incubated at 37° C./5% $CO_2$ for seven days in OPTI-MEM serum-free medium (Invitrogen, Carlsbad, Calif.). The medium was collected, centrifuged, filtered through 0.22 µm filtration system (Millipore, Billerica, Mass.), and then concentrated by a CENTRICON centrifuge filter (Millipore, Billerica, Mass.). Concentrated medium was mixed 1:1 with binding buffer (Pierce, Thermo Fisher Scientific, Rockford, Ill.), and subsequently loaded onto a pre-equilibrated protein A/G column (Pierce, Thermo Fisher Scientific, Rockford, Ill.) or HI-TRAP rProtein A FF (GE Healthcare, Waukesha, Wis.). The loaded column was washed with binding buffer and eluted with elution buffer (Pierce, Thermo Fisher Scientific, Rockford, Ill.). Eluted antibody was neutralized immediately and dialyzed against PBS buffer for overnight. Dialyzed antibody was concentrated with an AMICON centrifuge filter (Pierce, Thermo Fisher Scientific, Rockford, Ill.) and protein concentration was determined at OD280 nm with the extinct coefficient of 1.34 mg/mL. Purified antibody was analyzed using SDS-PAGE (Invitrogen, Carlsbad, Calif.), or protein LABCHIP (Caliper LifeSciences, Hopkinton, Mass.). SDS-PAGE was run under non-reducing conditions.

Example 6

Characterization of Affinity Matured 3B3 Antibodies

ELISA.

The selected anti-ADDL antibodies, i.e., those derived from the parental antibody, h3B3, where first assessed in a three-pronged Aβ ELISA to evaluate binding of the antibody to monomer Aβ, ADDLs, and fibrillar A. Polyclonal anti-ADDLs IgG (M90/1; Bethyl Laboratories, Inc., Montgomery, Tex.) was plated at 0.25 mg/well on IMMULON 3 REMOVAWELL strips (Dynatech Labs, Chantilly, Va.) for 2 hours at room temperature and the wells blocked with 2% BSA in TBS. Samples (monomeric Aβ, ADDLs, or fibrillar Aβ) diluted with 1% BSA in F12 were added to the wells, allowed to bind for 2 hours at 4° C., and washed 3× with BSA/TBS at room temperature. Monoclonal antibodies diluted in BSA/TBS were incubated for 90 minutes at room temperature and detected with a VECTASTAIN® ABC kit to mouse IgG. The HRP label was visualized with BIO-RAD peroxidase substrate and read at 405 nm on a Dynex MRX-TC microplate reader.

As shown in FIG. 1, with the exception of antibody 9.2, all of the anti-ADDL antibodies showed preferential binding to ADDLs relative to h3B3, selective (Comp 1 and 3: bind only ADDLs), non-selective (Comp 2: bind all forms of Aβ evaluated) comparators, and a control (no antibody). Antibody 9.2 showed low binding to all forms of Aβ, which suggested that its binding affinity was adversely affected during IgG conversion and/or antibody production. A summary of the ratio of ADDL:monomer and ADDL:fibrillar binding of the antibodies in this assay is presented in Table 7.

TABLE 7

| Antibody | ADDL:Monomer | ADDL:Fibrillar |
|---|---|---|
| h3B3 | 3.2 | 2.2 |
| 14.2 | 4.2 | 2.3 |
| 7.2 | 3.2 | 2.1 |
| 11.4 | 2.4 | 2.4 |
| 9.2 | 4.0 | 0.5 |
| 13.1 | 2.4 | 2.0 |
| 17.1 | 3.2 | 2.1 |
| 19.3 | 2.5 | 2.0 |

Figure 2:
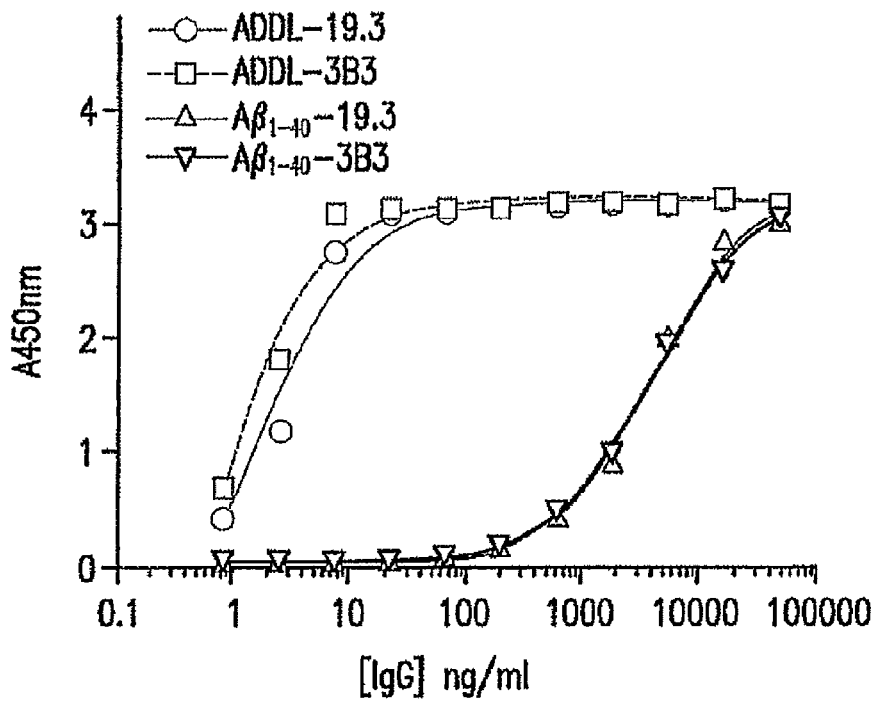
FIG. 2 is a graphic representation of the ELISA binding of anti-ADDL antibody 19.3 and antibody 3B3 to ADDLs or monomer Aβ (Aβ1-40) evaluated with an 11 point titration curve.

A full titration curve was generated for each antibody and h3B3 to determine their binding affinity for ADDLs, as compared with monomer Aβ. Biotinylated ADDLs (50 pmol/well) or monomer Aβ1-40 (100 pmol/well) were added to a high-capacity streptavidin-coated plate (Sigma-Aldrich, St. Louis, Mo.) and incubated for two hours at room temperature. The plates were washed in PBS with 0.05% TWEEN (six times) and then PBS alone (three times) prior to blocking wells with 5% non-fat dry milk in PBS for one hour at room temperature. The wells were then washed and a serial dilution of antibody samples added to the plates and allowed to bind for two hours at room temperature. After incubation and washing, the antibody binding was detected with a goat anti-human IgG-Fc secondary antibody conjugated to horse radish peroxidase (HRP) (1:1000; one hour at room temperature). The HRP label was visualized with tetramethyl benzidine (Virolabs, Chantilly, Va.) as a substrate and read at 450 nm on a microplate reader. This analysis confirmed that six of the seven affinity-matured antibodies showed preferential binding to ADDLs. See FIG. 2, which compares the preferential binding of h3B3 and 19.3 for ADDLs over monomeric Aβ1-40.

Cell-Based Binding Assay.

It has been shown that some anti-ADDL antibodies having preferential binding to ADDLs but cannot prevent ADDL binding to primary hippocampal neurons (Shughrue, et al. (2010) *Neurobiol. Aging* 31:189-202). To demonstrate that the anti-ADDL antibodies could block ADDL binding to neurons, a cell-based binding assay was carried out. Anti-ADDL antibodies were mixed with 500 nM bADDLs, with the final antibody concentrations ranging from 1.8 nM to 450 nM. As a control, the same concentration of heat-denatured antibody (98° C. for minutes) was mixed with bADDLs. The antibody-bADDL mixtures were incubated in siliconized microcentrifuge tubes (Fischer Scientific, Pittsburgh, Pa.) at 37° C. for one hour with constant end-to-end rotation at a low speed. The mixtures were then applied to primary hippocampal and/or cortical cultures and incubated at 37° C. for one hour. The incubation was terminated by removing the culture medium. Cells were subjected to fixation and post-fixation treatments. Cells were then incubated with streptavidin conjugated with alkaline phosphate (AP) at 4° C. overnight, washed five times with PBS and reacted with the TROPIX CDP-Star chemiluminescent substrate (Life Technologies, Carlsbad, Calif.) at room temperature for 30 minutes. The bADDL binding intensity was measured and recorded with an ENVISION microplate reader (PerkinElmer, Waltham, Mass.).

Figure 3:
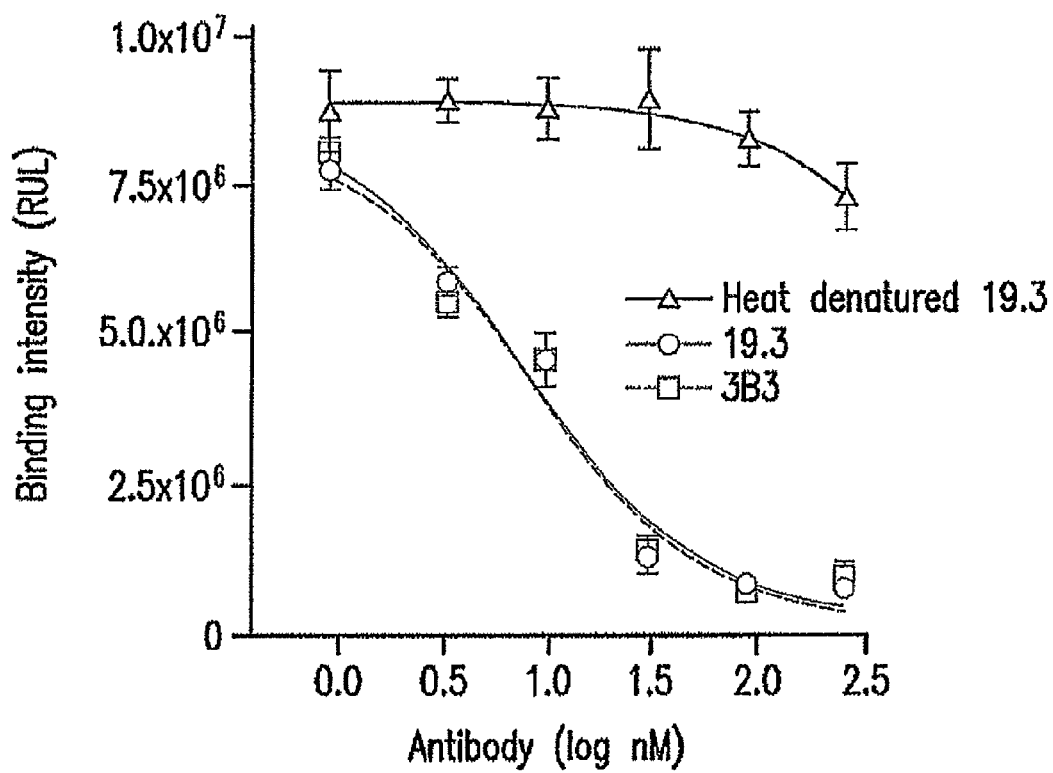
FIG. 3 is a graphic representation of the ability of anti-ADDL antibody 19.3 and 3B3 to block ADDL binding to primary hippocampal neuronal cells after pre-incubation with increasing concentration of the antibody. The ability of anti-ADDL antibody 19.3 to block ADDL binding to neurons was attenuated after heat denaturing of the antibody. Error bars represent standard error of the mean.

The results of this study showed that the anti-ADDL antibodies herein, specifically antibody 19.3, dramatically reduced ADDL binding to neurons (FIG. 3). However, a marked reduction in antibody activity in this assay was observed when the antibodies were heat-denatured (FIG. 3).

In Vitro FcRn Binding of Anti-ADDL Antibodies.

To characterize the ability of anti-ADDL antibodies to bind and dissociate immobilized human FcRn, the seven h3B3 variant anti-ADDL antibodies were evaluated in a BIACORE FcRn binding assay, a surrogate system used to evaluate antibody PK and predict the terminal half-life ($t_{1/2}$) of antibodies in non-human primates. Briefly, purified human FcRn protein was immobilized onto a BIACORE CM5 biosensor chip and PBSP (50 mM $NaPO_4$, 150 mM NaCl and 0.05% (v/v) TWEEN 20) pH 7.3 was used as running buffer. The monoclonal antibodies were diluted with PBSP, pH 6.0, to 100 nM, allowed to bind FcRn for 3 minutes to reach equilibrium and dissociated in pH 7.3 running buffer. A report point (Stability) was inserted at 5 seconds at the end of monoclonal antibody binding and the "% bound" was calculated as $RU_{stability}/RU_{binding}$ (%). This analysis indicated that monoclonal antibodies (mAbs) with identical Fc sequences but different Fab domains can bind and dissociate from FcRn with considerable differences.

Figure 4:
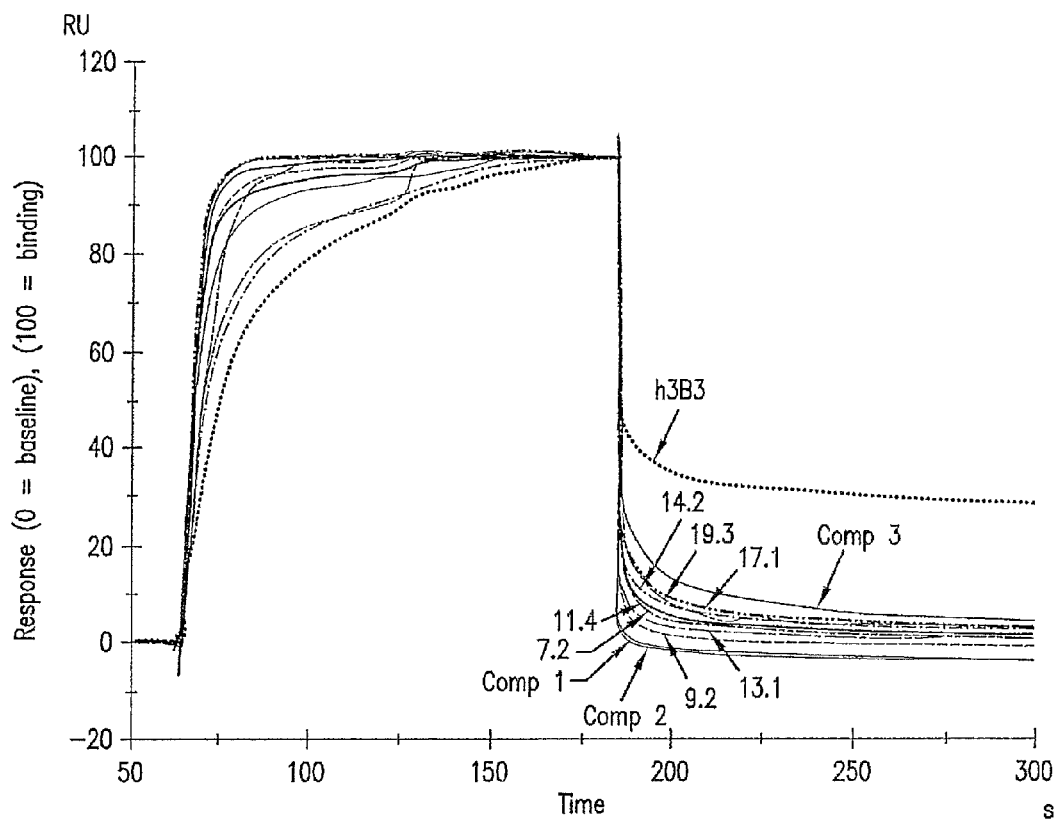
FIG. 4 is a graphic representation of the binding and dissociation of anti-ADDL antibodies to immobilized human FcRn when assessed with BIACORE (GE Healthcare, Piscataway, N.J.). The adjusted sensorgram shows initial binding at pH 6.0 and then the dissociation of antibodies at pH 7.3 from 180 seconds. A report point (Stability) was inserted at 5 seconds after the end of pH 6.0 binding and the "% bound" was calculated as $RU_{stability}/RU_{Binding}$ (%).

A comparison was made of the seven h3B3 variant anti-ADDL antibodies, along with h3B3, two ADDL preferring antibodies (Comp 1 and 3) and a non-selective (Comp 2: binds all Aβ forms evaluated) comparator in the FcRn binding assay. A sensorgram was generated (FIG. 4) showing the initial binding of the antibody at pH 6.0 and then the dissociation of the antibody at pH 7.3 from 180 seconds. As shown in FIG. 4, there was a noticeable difference between h3B3 and the other antibodies assessed. While h3B3 had a high percent bound to FcRn, the seven anti-ADDL antibodies of the present invention, as well as the two comparator antibodies exhibited considerably lower binding.

Example 7

Binding Affinity of Anti-ADDL Antibody 19.3

Affinity-matured antibody 19.3 was selected for further characterization. The complete DNA sequence and the deduced amino acid sequence for the variable region of the light chain was determined. BIACORE (GE Healthcare, Waukesha, Wis.) and KINEXA (Sapidyne, Boise, Id.) analyses were carried out to ascertain the binding affinity of anti-ADDL antibody 19.3 for ADDLs and determine the selectivity of 19.3 for ADDLs versus monomer Aβ. BIACORE- and KINEXA-based technologies are widely used for the measurement of binding affinity between macromolecules such as antibody and protein target.

BIACORE.

In the Surface Plasmon Resonance (SPR) technology on which BIACORE is based, quantitative measurements of the binding interaction between one or more molecules are dependent on the immobilization of a target molecule to the sensor chip surface. Binding partners to the target can be captured as they pass over the chip. SPR detects changes in mass in the aqueous layer close to the sensor chip surface by measuring changes in refractive index. When molecules in the test solution bind to a target molecule, the mass increases ($k_a$), when they dissociate the mass falls ($k_d$). This simple principle forms the basis of the sensorgram, i.e., a continuous, real-time monitoring of the association and dissociation of the interacting molecules. The sensorgram provides quantitative information in real-time on specificity of binding, active concentration of molecule in a sample, kinetics and affinity.

KINEXA.

The KINEXA technology (Sapidyne Instruments, Boise, Id.) measures binding constants to characterize biomolecular binding events in the solution phase, not binding events between a solution phase and a solid phase. In solution, the binding partners reach equilibrium after sufficient incubation. The unbound molecules are quantified with a titration, which reflects the portion of molecules bound to the partners. The KINEXA method does not require modification of molecules under study. With KINEXA, the reaction being measured occurs between unmodified molecules in solution. Therefore, concerns of how modification alters "native" binding reactions are eliminated. The KINEXA method allows a wider range of binding constants as tight as $10^{-13}$ M. The KINEXA software performs data analyses, which are based on exact solutions to classic binding equations ($K^d$ mathematics), not pseudo first-order approximations. KINEXA does not require arbitrary data manipulations or range selections.

As shown in Table 8, antibody 19.3 had a 4.8 nM affinity for ADDLs as compared to a 150 nM affinity for monomer Aβ in the BIACORE assay. The thirty-fold selectivity of antibody 19.3 for ADDLs over Aβ monomer was markedly better than that seen for the parental antibody, h3B3, which exhibited only a 10-fold preference for ADDLs versus Aβ monomer.

TABLE 8

| Antibody | ADDLs (nM) | Aβ1-40 (nM) | Ratio (Aβ monomer/ADDL) |
|---|---|---|---|
| 3B3 | 10.0 | 104.6 | ~10 |
| 19.3 | 4.8 | 150.0 | ~31 |

Similarly, antibody 19.3 was evaluated in a KINEXA-based equilibrium constant measurement. As shown in Table 9, antibody 19.3 had an equilibrium constant of 2.7 nM, which represents more than a six-fold preference for ADDL oligomers versus Aβ40 monomer binding in the same assay.

TABLE 9

| Antibody | ADDLs (nM) | Aβ1-40 (nM) | Ratio (Aβ monomer/ADDL) |
|---|---|---|---|
| 3B3 | 3.3 | 45.0 | ~13.6 |
| 19.3 | 2.7 | 16.7 | ~6.2 |

$EC_{50}$ of 19.3 for Aβ Oligomers and Aβ1-40 in One-Sided ELISA Assay.

Figure 5A:
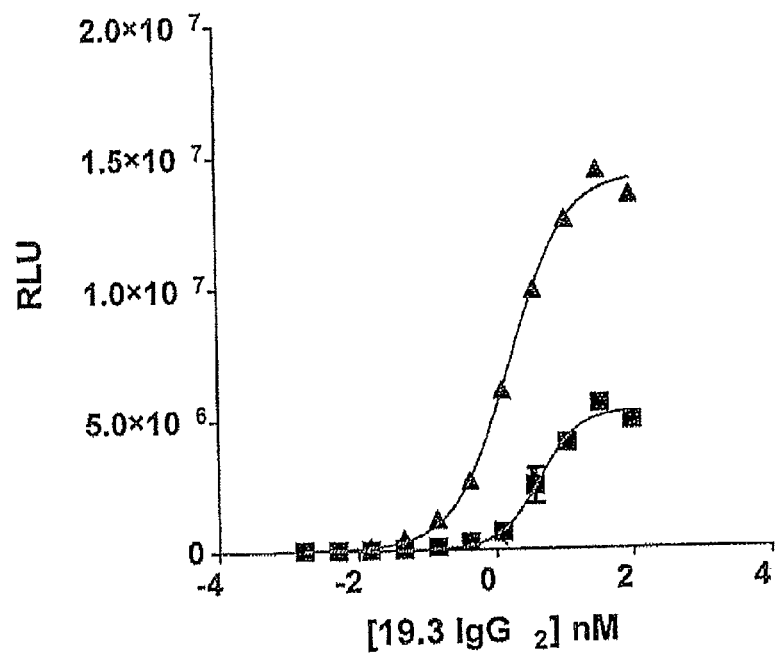
FIG. 5A shows a one-sided ELISA with plates coated with either Aβ oligomer (triangles) or Aβ monomer (squares), demonstrating the relative affinities and maximum binding characteristics of the humanized antibody 19.3.

$EC_{50}$ represents the half-maximal total Aβ oligomer binding. High protein binding plates were coated at either 100 pmol/well Aβ1-40 or 50 pmol/well Aβ oligomers in PBS, overnight at 4° C. Next day, plates were washed five times with PBS+0.05% TWEEN 20 and blocked overnight with casein blocking buffer (Thermo Scientific, Waltham, Mass.) and 0.05% TWEEN 20. The 19.3 antibody was tested at 0 to 15 µg/ml in a 12-point three-fold dilution series. After two hours at room temperature incubation, the plates were washed and alkaline phosphatase-conjugated anti-human IgG (ThermoScientific, Waltham, Mass.) was added at 0.08 μg/ml. After incubation for 45 minutes at room temperature, the plates were washed and TROPIX CDP star (Applied Biosystems, Foster City, Calif.) was added. Luminescence was detected after minutes on an ENVISION plate reader (PerkinElmer, Waltham, Mass.). Curve fits were completed using GraphPad Prism (GraphPad Software, Inc., San Diego, Calif.) software. This analysis indicated that the 19.3 antibody (IgG2 isotype) has an $EC_{50}$ of approximately 1.6 nM and 4.3 nM for Aβ oligomers and Aβ1-40 monomer, respectively, in the one-sided ELISA assay (FIG. 5A). In this format the 19.3 antibody demonstrated approximately three-fold greater maximum binding for Aβ oligomers as compared to Aβ40 monomer, while the potency was approximately 3.7-fold greater.

Competitive Binding Assays with Aβ Oligomers and Aβ Monomer.

To more accurately represent an in vivo CSF sample, where both Aβ oligomers and Aβ monomers would be present, the affinity of 19.3 for Aβ oligomers in the presence of Aβ1-40 monomer was tested in a competitive ELISA format.

The ELISA plate was prepared by first coating with a preparation of Aβ oligomers at 50 pmol per well and then adding the 19.3 antibody at a final concentration of 2 nM to each well. This concentration of 19.3, i.e., 2 nM, represents the $EC_{50}$ concentration for Aβ oligomers binding determined in the one-sided ELISA (FIG. 5A). Adding Aβ1-monomer in a titration curve to competitively remove 19.3 from the Aβ oligomer-coated surface resulted in an EC50 of 5.5 μM. Aβ1-40 monomer-coated plates were prepared in the same way, using 100 pmol/well. The 19.3 antibody was applied at 4 nM to each well in the casein blocking buffer matrix and allowed to interact with Aβ oligomers or Aβ1-40 for 30 minutes at room temperature with shaking. A 12-point, three-fold concentration curve starting at 10 μM, for either Aβ oligomers or Aβ1-40, was applied to the antibody containing wells. For plates coated with Aβ oligomers, Aβ1-40 was added to the wells; for Aβ1-40 plates, Aβ oligomers were added to the wells. The plates were incubated for one and half hours at room temperature. Both detection of residual antibody binding and the $EC_{50}$ calculations were determined as in the one-sided ELISA assay.

Figure 5B:
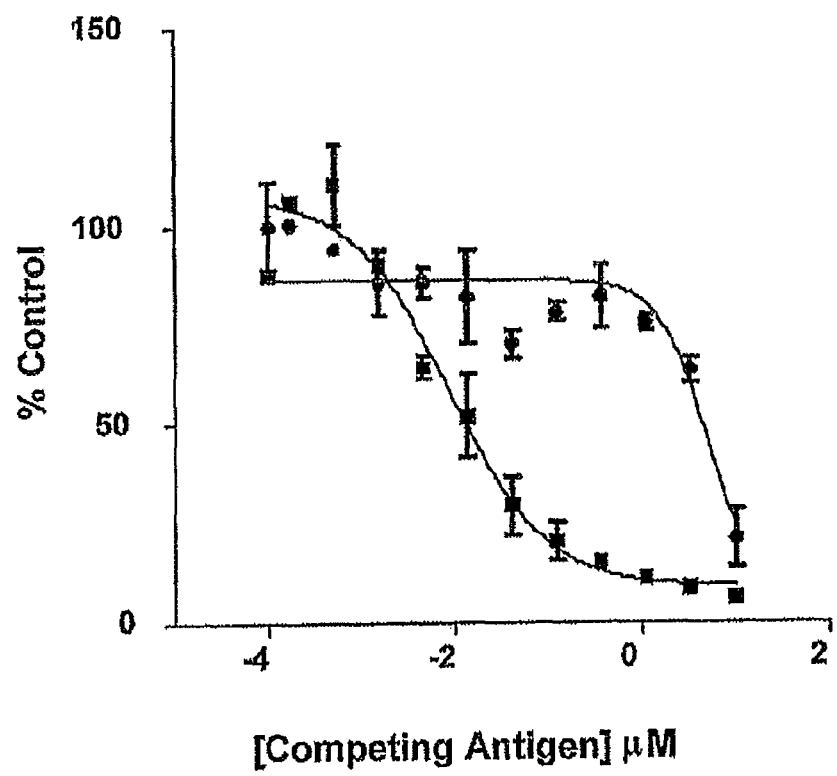
FIG. 5B shows a competitive ELISA and the relative affinities of 19.3 for Aβ oligomers (triangles) and Aβ monomer (squares) coated on an ELISA plate in the presence of the competing species in solution.

This analysis indicated that adding Aβ1-40 monomer in a titration curve to competitively remove 19.3 from Aβ oligomer-coated surface resulted in an $EC_{50}$ of 5.5 μM (FIG. 5B). When 100 pmol per well of Aβ1-40 monomer was used to coat the ELISA plate and Aβ oligomers were used to compete for antibody binding, the $EC_{50}$ was 8.7 nM. This indicated that 19.3 had an affinity for Aβ1-42 oligomers compared to Aβ1-40 monomers of ~630:1 in a competitive binding assay. Alternatively stated, the concentration of Aβ1-40 required to displace 50% of 19.3 from Aβ oligomers was approximately 600-fold higher than the concentration of Aβ oligomers required to displace 19.3 binding to Aβ1-40. Concentrations up to 0.2 pM of Aβ oligomers have been reported in CSF from AD patients (Georganopoulou, et al. (2005) *Proc. Natl. Acad. Sci. USA* 102:2273-2276) as compared to 1500 pM of Aβ monomer. Thus, the sensitivity and selectivity of 19.3 for Aβ oligomers indicated a potential utility in a sandwich ELISA to detect Aβ oligomers above background levels of Aβ monomer.

ALPHALISA Assay.

The ALPHALISA technology (PerkinElmer) is a bead-based immunoassay designed for the detection of analytes in biological samples. This chemiluminescent assay exhibits remarkable sensitivity, wide dynamic range and robust performance that compares advantageously with conventional ELISA. The selectivity and sensitivity the 19.3 antibody for ADDLs versus monomeric Aβ (Aβ1-40) in the ALPHALISA assay was determined. This analysis indicated that a signal at 0.2 pM of ADDLs was greater than a signal at 1000 pM of Aβ1-40, indicating an ADDL versus monomeric Aβ selectivity of approximately 5000 in this assay.

Immunohistochemistry.

Immunohistochemical analysis of tissues from Tg2576 mice indicated that the 19.3 antibody did not bind vascular plaques, exhibited essentially no binding to dense core plaques and no plaque clearance in Tg2576 mice.

Example 8

Biophysical Characterization of Anti-ADDL Antibody 19.3

Biophysical characterization to assess the potential for antibody aggregate formation was carried out to show that the anti-ADDL antibodies were stable under various conditions. Anti-ADDL antibody 19.3 was concentrated to >50 mg/mL and placed in a number of formulations with a pH ranging from 5.0 to 8.0. Two sets of samples were incubated at 37° C. and 45° C. for one week. A third set of samples was placed at −70° C. to initiate a series of five freeze/thaw cycles. Size exclusion chromatography analysis indicated that the antibody preparations were predominantly (>95%) in the monomer state, with a small amount of dimers, which is typical for monoclonal antibody preparations. The amount of dimers and higher molecular weight oligomers did not increase after the temperature stress across all buffers and no fragmentation was observed. As summarized in Table 10, the near ultraviolet turbidity analysis also indicated lack of aggregation. The freeze/thaw stressed samples showed buffer-dependent increase in turbidity, which was comparable to other monoclonal antibodies. Viscosity at 50 mg/mL was below 2 centipoise. Differential scanning calorimetry also revealed acceptable thermal stability, with Fab unfolding at about 72° C. and the least stable CH2 domain unfolding above 65° C. Taken together, antibody 19.3 demonstrated very good structural stability.

TABLE 10

| Antibody | Initial Aggregates (%) | Initial Fragments (%) |
|---|---|---|
| 19.3 | 2.2 | 0.0 |
| Control 1 | 1.6 | 0.4 |
| Control 2 | 2.6 | 0.0 |

Example 9

Preparation of 19.3 Variants

An assessment of the amino acid sequence of the 19.3 antibody was conducted to identify potential sites of deamidation. Asparagine and aspartic acid residues present in the CDRs of therapeutic antibodies can undergo deamidation and isoaspartate formation (Valsak & Ionescu (2008) *Curr. Pharm. Biotech.* 9:468-481; Aswad, et al. (2000) *J. Pharm. Biomed. Anal.* 21:1129-1136), the formation of which can alter the binding potency of an antibody and, in turn, reduce antibody effectiveness for use as a therapeutic. Therefore, the asparagine residue at position 33 of the light chain CDR1 of antibody 19.3 was altered. Variants of the 19.3 antibody were produced (Table 11) with the substitution of serine, threonine or glutamic acid for the asparagine at position 33 in CDR1. The substitution of aspartic acid for the asparagine as position 33 was also generated as a control.

The mutagenesis of the asparagine at position 33 (N33) of the light chain CDR1 for the antibody 19.3 into N33S, N33T, N33E, or N33D was carried out by site-directed mutagenesis from the wild-type expression vector of pVlJASN-GS-19.3-LCK using QUIKCHANGE IT XL Site-Directed Mutagenesis Kit (Agilent Technologies, La Jolla, Calif.). The codon AAT for N was mutated to AGT for S in 19.3 N33S, ACT for T in 19.3 N33T, GAA for E in 19.3 N33E, or GAT for D in 19.3 N33D. Additional mutations at the asparagine at position 35 (N35) of CDR1 were also generated and combined with the N33S mutation (Table 11). Furthermore, mutations at the asparagine at position 58 in the CDR2 of antibody 19.3 were prepared (Table 12). All new codons in were confirmed by DNA sequence analysis. To generate full-length IgG antibodies for these variants, the respective light chain plasmids were paired with the cognate heavy chain plasmid, pVlJNSA-19.3-HCG2, for transient transfection in 293 FREESTYLE cells (Invitrogen, Carlsbad, Calif.). The expression and purification methods were described above.

Table 11 summarizes the amino acid sequence of CDR1 of the light chain of the variants compared to the CDR1 of the light chain for the parental antibody, 19.3. The present invention provides the variants of 19.3 whose light chain CDR1 is as set out in Table 11 below and whose CDR2 and CDR3 light chains and all heavy chains are as set for 19.3 itself.

TABLE 11

| Antibody | LC-CDR1 Sequence | SEQ ID NO: |
|---|---|---|
| 19.3 (parental) | RSSQSIVHSNGNTYLE | 14 |
| 19.3 N33S | RSSQSIVHSSGNTYLE | 46 |
| 19.3 N33T | RSSQSIVHSTGNTYLE | 47 |
| 19.3 N33A | RSSQSIVHSAGNTYLE | 48 |
| 19.3 N33E | RSSQSIVHSNGNTYLE | 49 |
| 19.3 N33D | RSSQSIVHSDGNTYLE | 50 |
| 19.3 N33S-N35Q | RSSQSIVHSSGQTYLE | 51 |
| 19.3 N33S-N35S | RSSQSIVHSSGSTYLE | 52 |
| 19.3 N33S-N35T | RSSQSIVHSSGTTYLE | 53 |
| 19.3 N33S-N35A | RSSQSIVHSSGATYLE | 54 |

Table 12 summarizes the amino acid sequence of CDR2 of the light chain of the variants compared to the CDR2 of the light chain for the parental antibody, 19.3. The present invention provides the variants of 19.3 whose light chain CDR2 is as set out in Table 12 below and whose CDR1 and CDR3 light chains and all heavy chains are as set for 19.3 itself.

TABLE 12

| Antibody | LC-CDR2 Sequence | SEQ ID NO: |
|---|---|---|
| 19.3 (parental) | KASNRFS | 15 |
| 19.3 N58Q | KASQRFS | 55 |
| 19.3 N58S | KASSRFS | 56 |
| 19.3 N58T | KASTRFS | 57 |
| 19.3 N58A | KASNRFS | 58 |

The 19.3 variants were subsequently evaluated to determine whether the mutations had any effect on the stability of the antibody. Aliquots of purified variant antibodies, along with the 19.3 parental antibody, were incubated under various conditions at 4° C., 25° C. or 40° C. for a month before being subjected to ELISA analysis. High protein binding plates (Costar, Corning, Lowell, Mass.), were coated with target ligand in PBS overnight at 4° C. The concentration of coating protein was 50 pmol/well for ADDLs. ADDLs were generated as described in Example 1. One the next day, plates were washed five times with PBS+0.05% TWEEN 20 (Sigma Aldrich, St. Louis, Mo.) and blocked overnight with casein blocking buffer (Thermo Scientific, Waltham, Mass.) and 0.05% TWEEN 20. Three representative antibodies, 19.3, 19.3 N33S, and 19.3 N33T were tested at 15 µg ml to 0 µg/ml in a 12-point three-fold dilution series. After 2 hours at room temperature incubation, the plates were washed and alkaline phosphatase-conjugated anti-human IgG (ThermoScientific, Waltham, Mass.) was added at 0.08 µg/ml. After 45 minutes at room temperature incubation, the plates were washed and TROPIX CDP-Star chemiluminescent substrate (LIFE TECHNOLOGIES, Carlsbad, Calif.) was added. Luminescence was detected after 30 minutes on an ENVISION microplate reader (PerkinElmer, Waltham, Mass.). Curve fits were completed using GRAPHPAD PRISM software (GraphPad Software, Inc., San Diego, Calif.).

Figure 6A:
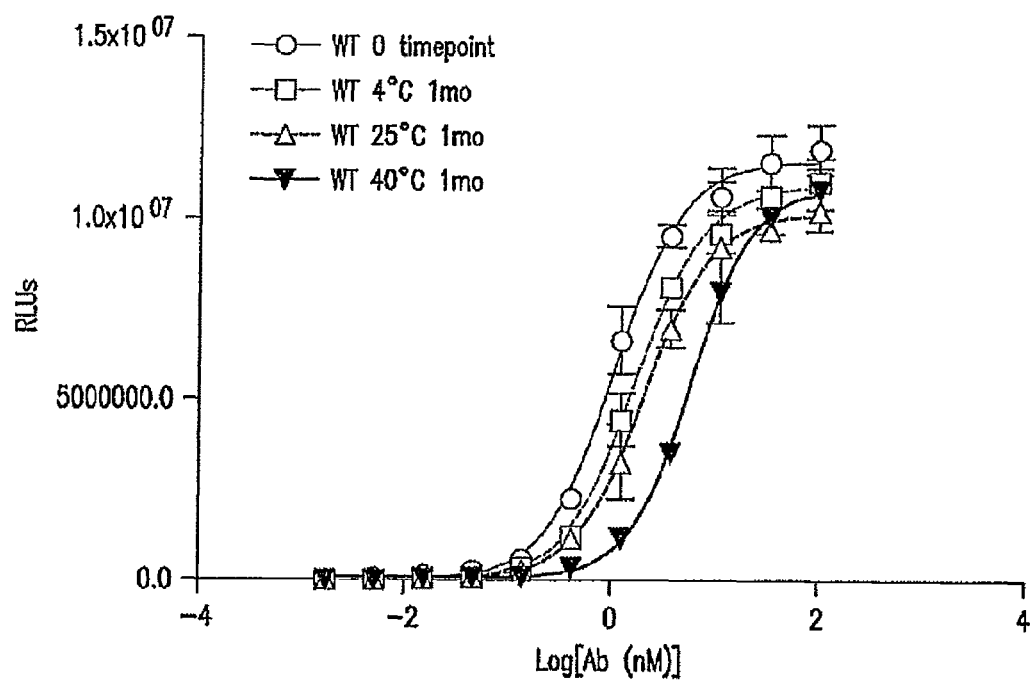
FIGS. 6A-6C are graphic representations of the ELISA binding to ADDLs of the anti-ADDL antibody 19.3 (designated as WT in FIG. 6A) and two 19.3-derived anti-ADDL antibodies (FIGS. 6B and 6C) after incubation up to one month at varying temperatures to evaluate antibody stability. The 19.3-derived anti-ADDL antibodies were composed of a single amino-acid substitution of Asn33 within light chain CDR1 to either Ser33 (N33S.
Figure 6B:
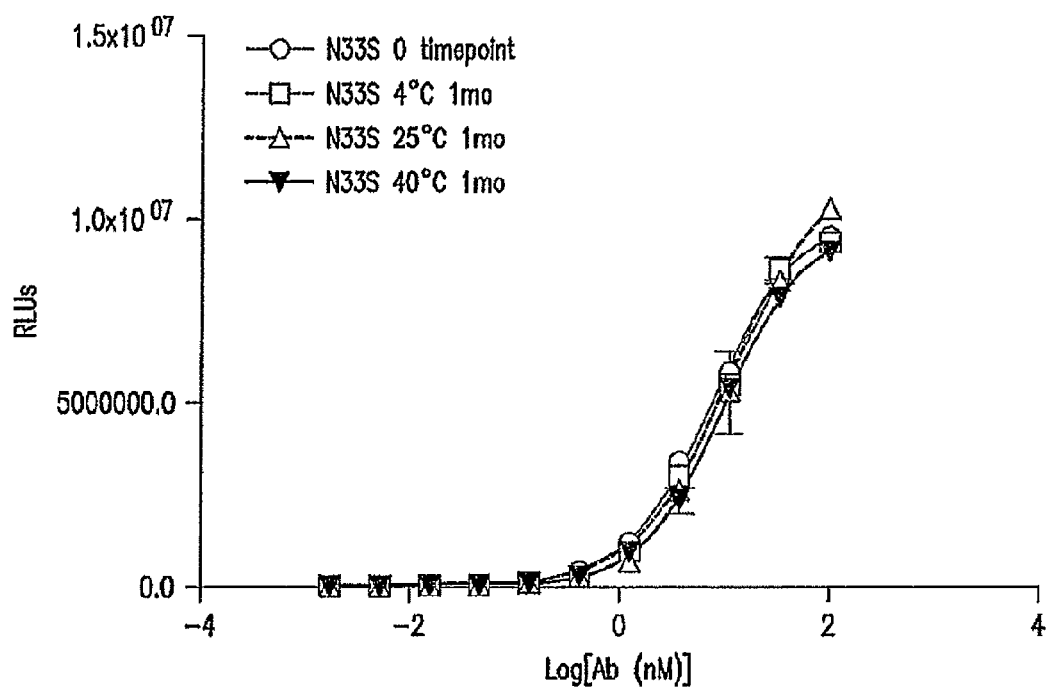
Figure 6C:
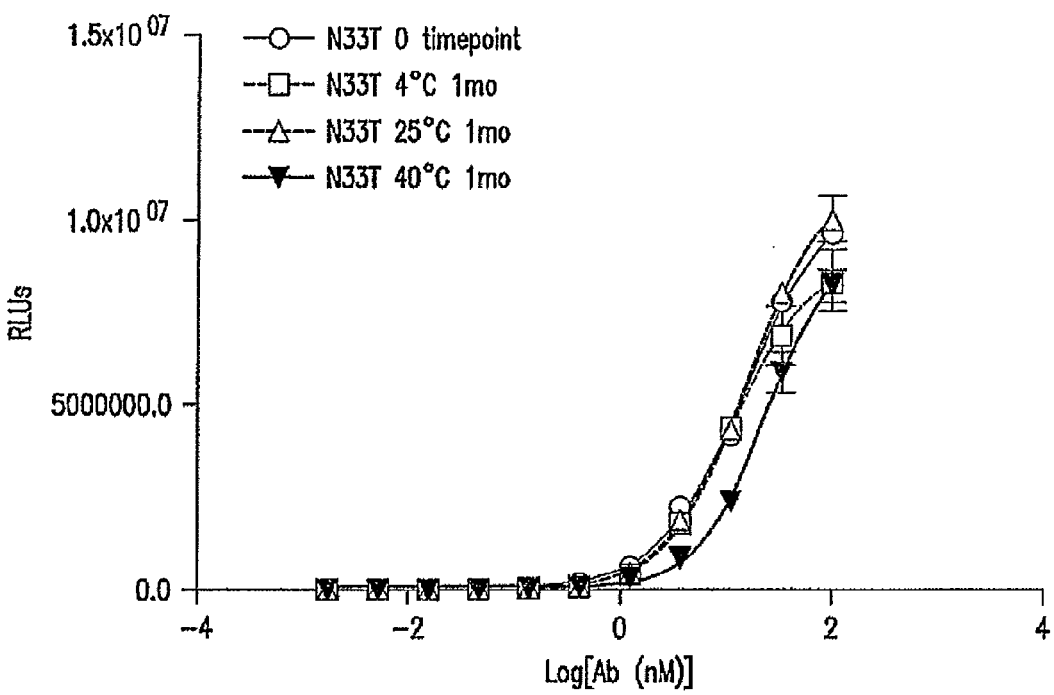

As shown in FIGS. 6B and 6C, antibodies 19.3 N33S and 19.3 N33T had enhanced binding stability compared to the 19.3 parent (WT, FIG. 6A) following a one-month incubation at varying temperatures. A summary of the $EC_{50}$s of these antibodies at the various incubation temperatures is provided in Table 13.

TABLE 13

| | | Antibody $EC_{50}$ (nM) | | |
|---|---|---|---|---|
| Antigen | Incubation | 19.3 | 19.3 N33T | 19.3 N33S |
| bADDL | 0 timepoint | 1.1 | 15.5 | 7.8 |
| | 4°, 1 month | 1.7 | 11.6 | 8.6 |
| | 25°, 1 month | 2.1 | 15.7 | 12.8 |
| | 40°, 1 month | 5.9 | 23.5 | 10.1 |
| Aβ1-40 | 0 timepoint | 10.1 | 332.1 | 55.1 |
| | 4°, 1 month | 16.3 | 306.8 | 59.1 |
| | 25°, 1 month | 22.1 | ND | 24.3 |
| | 40°, 1 month | 88.8 | 96.3 | 29.9 |

$EC_{50}$s of several of the 19.3 variants were determined and it was found that the variants maintained specificity for ADDLs in an ELISA assay (Table 14)

TABLE 14

| | $EC_{50}$ (nM) | |
|---|---|---|
| Antibody | ADDL | Aβ1-42 |
| 19.3 | 0.8 | 18 |
| 19.3 N33S | 1.7 | 150 |
| 19.3 N33T | 3.1 | 244 |
| 19.3 N33D | 0.82 | 28 |

All antibodies were IgG2.

Example 10

Aβ Oligomer Preferring Antibodies in Aβ Oligomer-Selective Sandwich ELISA

Figure 7A:
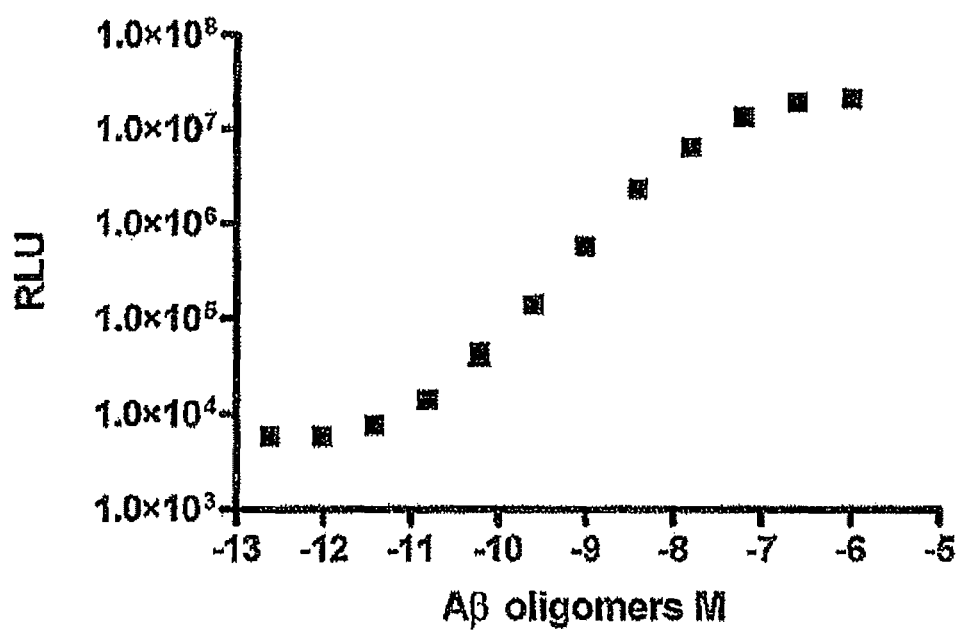
FIGS. 7A-7C are graphic representations showing the sensitivity of three pairs of antibodies in a sandwich ELISA format using chemiluminesence (ENVISION Multilabel Reader, Perkin Elmer, Waltham, Mass.), as the detection method and their relative affinities for Aβ oligomers.

In a screen of capture and detecting antibody pairs in a sandwich ELISA format, the combination of 19.3 as the capture antibody with either 7305, an anti-Aβ oligomer antibody (20C2, U.S. Pat. No. 7,780,963, which is incorporated herein by reference in its entirety) or 82E1 (Immunobiological Laboratories (IBL), Inc., Minneapolis, Minn.) performed comparably in casein blocking buffer in an Aβ oligomer standard curve, each giving a limit of detection (LoD) under 4 pg/mL (FIG. 7A). Use of an anti-Aβ monomer antibody as both capture and detection antibody has been reported as an Aβ oligomer assay, however, absolute levels of sensitivity or selectivity were either not reported (6E10/6E10; Gandy, et al. (2010) *Ann. Neurol.* 68:220-230), or selectivity was below that desired for an assay to measure Aβ oligomers in human CSF (82E1/82E1; Xia, et al. (2009) *Arch. Neurol.* 66:190-199).

Figure 7B:
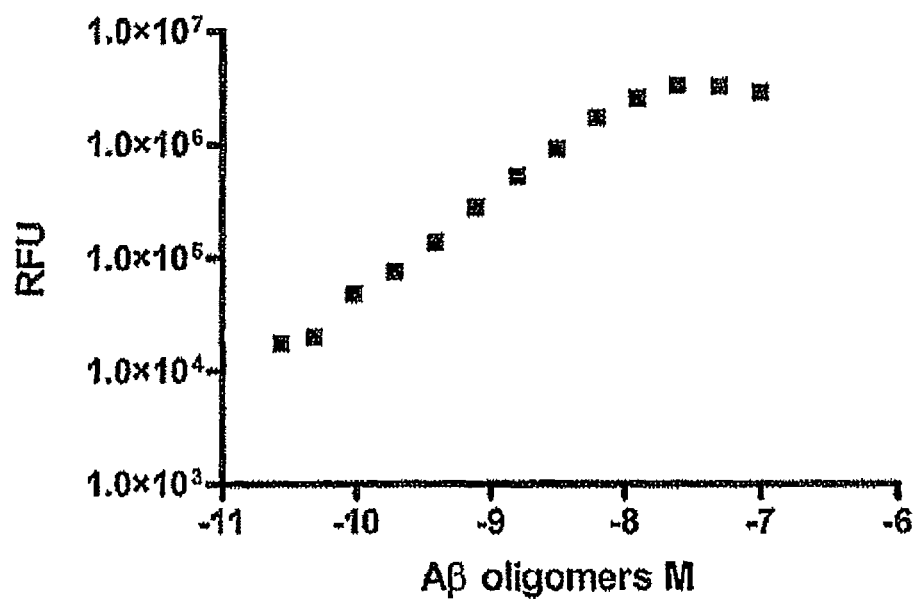
Figure 7C:
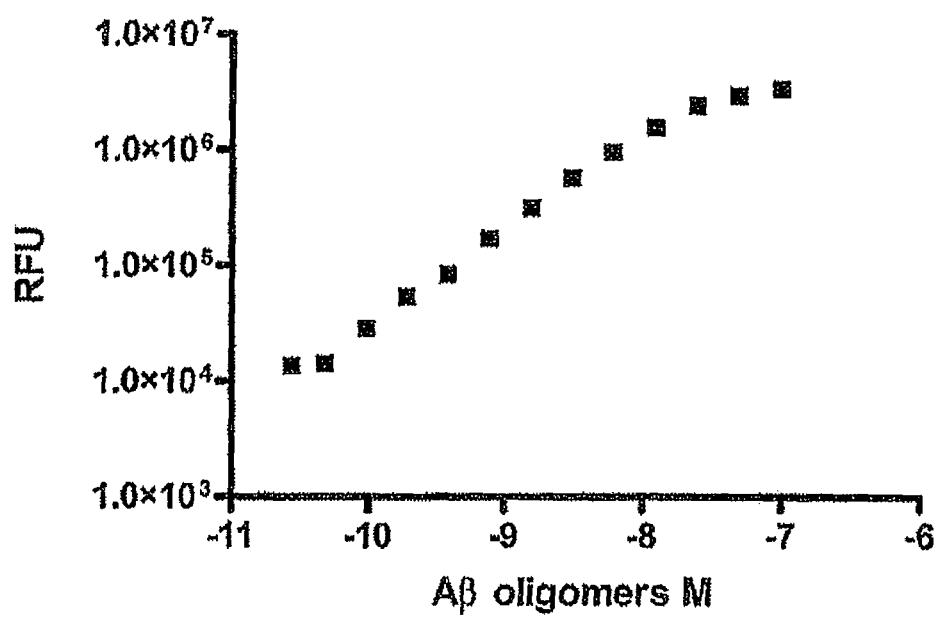

To determine the sensitivity of 6E10 and 82E1, these antibodies were used in sandwich ELISA assays. In this analysis, identical antibodies were used for both capture and detection antibodies, e.g., 6E10/6E10 (FIG. 7B) and 19.3/19.3 (FIG. 7C), as well as sandwich ELISA assay pairs using 19.3 as a capture antibody only (FIG. 7A, with 82E1 detection). This analysis indicated that 6E10/6E10 and 19.3/19.3 both demonstrated approximately one hundred fold reduced sensitivity compared to either 19.3/7305 or 19.3/82E1.

The 19.3/82E1 ELISA utilizing luminescence detection technology (ENVISION Multilabel plate reader, PerkinElmer, Waltham, Mass.) (FIG. 7A), generated a LoD of approximately 1.3 pg/mL. In this assay format, the lower limit of reliable quantification (LLoRQ) of Aβ oligomer was 4.2 pg/mL (with coefficients of variance less than 20% at this lowest measure) and the assay was approximately 1000 fold-selective for Aβ oligomer signal as compared to Aβ40 monomers. While this assay was used to evaluate Aβ oligomer preparations, it may not be sensitive enough to reliably detect Aβ oligomer levels in human CSF at levels suggested by previous estimates (Georganopoulou, et al. (2005) *Proc. Natl. Acad. Sci. USA* 102:2273-2276).

Example 11

Aβ Oligomer-Selective Sandwich ELISA with Improved Sensitivity

Both the 19.3 and 7305 (19.3×7305) and the 19.3 and 82E1 (19.3×82E1) antibody pairs were evaluated in a sandwich ELISA using a paramagnetic microparticle detection immunoassay system, ERENNA Immunoassay System (SINGULEX, Almeda, Calif.) to determine if assay sensitivity could be improved further for the measurement of Aβ oligomers in human and non-human primate fluid samples.

Capture Antibody Labeling.

Binding of the capture antibody to DYNABEADS (microparticle (MP) beads) was achieved by removing supernatent from 50 μl of DYNABEADS using a magnet. The DYNABEADS were resuspending in 200 μl of an antibody binding and washing buffer, e.g., RIPA buffer (Cell Signaling Technologies, Beverly, Mass.), containing 5 μg of the capture antibody. The mixture was incubated for 10 minutes with rotation at room temperature. The supernatent was removed from capture antibody/MP bead complex with a magnet. The complex was washed with 200 μl of the binding and washing buffer.

Coupling of Capture Antibody to DYNABEADS (MP Beads).

The capture antibody-coupled MP beads (5 μg 19.3/50 μl MP bead complex) were washed twice in 200 μL of the conjugation buffer (20 mM sodium phosphate, 0.15 M NaCl (pH 7-9)), placed on a magnet and the supernatant was discarded. The capture antibody/MP beads were resuspended in 250 μl 5 mM BS3 solution (Bis(sulfosuccinimidyl) suberate in conjugation buffer). The resuspended beads were incubated at room temperature for 30 minutes with tilting/rotation. The cross-linking reaction was quenched by adding 12.5 μl of a quenching buffer (1M Tris-HCl, pH 7.5) and subsequently incubated at room temperature for 15 minutes with tilting/rotation. The cross-linked MP beads were washed three times with 200 μl PBS-T. The MP beads were diluted to 100 μg/mL in assay buffer for use in the assay protocol.

Detection Antibody Labeling.

ALEXA FLUOR 546 (Invitrogen, Carlsbad, Calif.) was coupled to the detection antibody according to the manufacturer's protocol. Briefly, detection antibody was diluted to 1 mg/mL and one-tenth volume of 1M sodium bicarbonate buffer was added. This solution of detection antibody (100 μL) was added to the vial of ALEXA FLUOR 546 dye, and the vial was capped, gently inverted to dissolve the dye and stirred at room temperature for 1 hour. The columns were spun to separate any unlabeled fluorescent tag from the detection antibody and the antibody was loaded onto a Component C (BIOGEL P-30, BioRad, Hercules, Calif.) fine size exclusion purification resin. After the gel buffer drained away, 100 μL detection antibody and dye reaction volume were added onto the center of the resin at the top of the spin column and absorbed into the gel bed. To the column was slowly added, at room temperature, 100 μL of an elution buffer (0.01 M potassium phosphate, 0.15 M NaCl, pH 7.2, with 0.2 mM sodium azide). Additional elution buffer was added and as the column ran, the column was illuminated to visualize the front of the dyed/tagged antibody. The first column dye line was the labeled antibody. Free dye remained in the column bed and was discarded with the spin column.

The Aβ oligomer sandwich ELISA was carried out using a paramagnetic microparticle-based immunoassay platform (ERENNA immunoassay system, SINGULEX, Almeda, Calif.) to determine oligomer levels in CSF samples or Aβ oligomer standards. Microparticles (MPs) for capture were prepared by binding 12.5 μg of the capture antibody per mg of MPs. The capture antibody-bound MPs were diluted to 100 μg/mL in assay buffer (Tris buffer with 1% TRITON X-100, d-desthiobiotin, 0.1% bovine serum albumin) and added at 100 μL to 100 μL of CSF sample or standards (diluted in Tris buffer and 3% bovine serum albumin), followed by incubation for two hours at 25° C. The MPs were retained via a magnetic bed, and unbound material was removed in a single wash step using assay diluent using the THYDROFLEX plate washer (Tecan, Männedorf, Switzerland). The ALEXA FLUOR-labeled detection antibody was diluted to a final concentration of 500 pg/mL and filtered through a 0.2 μm filter (Pall 4187, Fort Washington, N.Y.). The detection antibody was added to 20 μL/well of individual sample particles. The ELISA plates were incubated for one hour at 25° C., while shaking in a Jitterbug (Boekel, Feasterville, Pa.). The wells were washed four times with assay buffer to remove any unbound detection reagent. MP/capture antibody/Aβ oligomer/detection antibody complexes were transferred to a new plate, buffer was aspirated off and 10 μL/well of elution buffer was added, followed by a 5 minute incubation at 25° C., while shaking in a Jitterbug at speed 5. Eluted, fluor-labeled detecting antibody was transferred to a 384 plate containing 10 μL/well neutralization buffer and read on a paramagnetic microparticle detector (ERENNA, SINGULEX, Alameda, Calif.) at 60 seconds per well read time.

While paramagnetic microparticle immunoassays, such as the ERENNA Immunoassay System, have been used for biomarkers present in a biological sample in the nanomolar (nM) range, as observed for Aβ1-40 and Aβ1-42, it has not been previously demonstrated for as an immunoassay system that can specifically and reliably detect a biomarker present in a CSF sample in the femtomolar (fM) range, such as with Aβ oligomers. Without wishing to be bound by any theory, it is believed, and has demonstrated, that the specificity and sensitivity of the assays herein are attributable to the specificity and sensitivity of the anti-ADDL antibody pair selected and used in the sandwich ELISA. Similarly, while the ERENNA Immunoassay System is used herein to illustrate the claimed assay, it is possible that other detection systems having comparable sensitivities could be employed in the inventive methods.

The 19.3×7305 sandwich ELISA was conducted using the ERENNA Immunoassay System (SINGULEX, Almeda, Calif.), covalently-coupling the 19.3 antibody to the ERENNA microparticle (MP) beads (hereinafter "19.3/MP beads"). The 19.3/MP beads were then mixed with buffer containing a standard curve of either Aβ oligomer or monomeric Aβ40. The resulting 19.3/MP bead/Aβ oligomer or Aβ40 complex (hereinafter "Aβ oligomer complex") was washed and either a fluorescently-tagged 7305 or 82E1 detection antibody was bound to the Aβoligomer complex. The ERENNA instrument, using a proprietary detection technology capable of single-molecule counting (see U.S. Pat. No. 7,572,640), measured the fluorescently-labeled detection antibody following its release from the sandwich ELISA. As shown in Table 15, data from the 19.3×7305 assay, using a two-fold dilution of the Aβ oligomer standard in buffer, aligned with a linear two-fold dilution of fluorescent signal (detected events mean). Signals generated by neat rhesus CSF, or CSF to which a standard curve of Aβ oligomers was introduced, demonstrated that the fluorescent signal attributed to binding of the tagged 7305 antibody was equivalent in both cases, while the 19.3×82E1 sandwich assay was able to detect spiked Aβ oligomers across the full standard curve. In the assay format using 7305 as the detection antibody, this was indicative that there was a non-specific background (from something present in the rhesus CSF) saturating over the range of the Aβ oligomers dilution series that was sufficient to detect Aβ oligomers in buffer alone. Subsequently, the fluorescent signal was found to be identical to that for a naked microparticle, even in the absence of the 19.3 antibody coupling, which was also consistent with a non-specific signal due to 7305 antibody cross-reactivity.

TABLE 15

| Standard Diluent | Expected [ADDLs] pM | DE Mean | SD | CV % | Interp [ADDLs] pM Mean | SD | CV % | % Recovery |
|---|---|---|---|---|---|---|---|---|
| Standards Diluent | 5.00 | 5579 | 506 | 9 | 5.1 | 0.5 | 10 | 103 |
|  | 1.67 | 1942 | 235 | 12 | 1.7 | 0.2 | 13 | 100 |
|  | 0.56 | 691 | 152 | 22 | 0.5 | 0.1 | 25 | 96 |
|  | 0.19 | 324 | 43 | 13 | 0.2 | 0.1 | 17 | 116 |
|  | 0.06 | 131 | 34 | 26 | 0.1 | 0.1 | 49 | 88 |
|  | 0.00 | 72 | 28 | 39 | ND |  |  |  |
| Rhesus CSF-Depleted | 5.00 | 9097 | 88 | 1 |  |  |  |  |
|  | 1.67 | 9112 | 195 | 2 |  |  |  |  |
|  | 0.56 | 8721 | 166 | 2 |  |  |  |  |
|  | 0.19 | 8785 | 269 | 3 |  |  |  |  |
|  | 0.06 | 8744 | 273 | 3 |  |  |  |  |
|  | 0.00 | 8678 | 519 | 6 |  |  |  |  |
| Rhesus CSF-Non-Depleted | 5.00 | 10353 | 237 | 2 |  |  |  |  |
|  | 1.67 | 9719 | 495 | 5 |  |  |  |  |
|  | 0.56 | 9902 | 546 | 6 |  |  |  |  |
|  | 0.19 | 9971 | 319 | 3 |  |  |  |  |
|  | 0.06 | 9721 | 329 | 3 |  |  |  |  |
|  | 0.00 | 10515 | 282 | 3 |  |  |  |  | n = 3 for each experiment.

Figure 8:
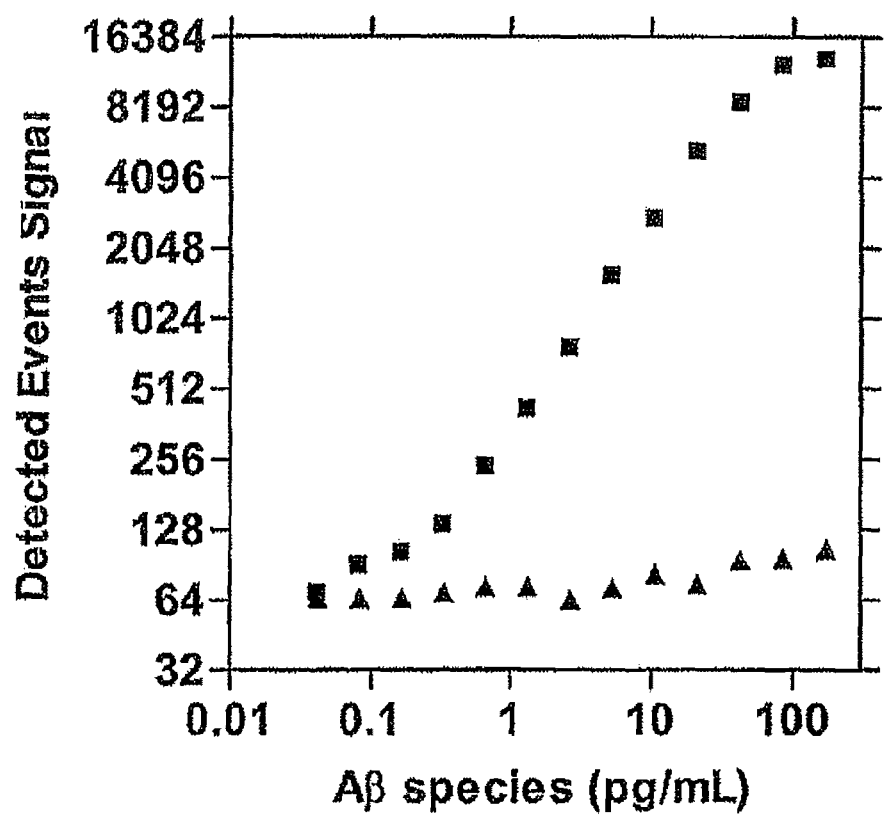
FIG. 8 is a graphic representation of the sensitivity and selectivity for the detection of Aβ oligomers (squares) as compared to Aβ monomer (triangles) using the anti-Aβ oligomer antibodies 19.3 and 82E1 as measured using a paramagnetic microparticle detector, such as the ERENNA digital detector (SINGULEX, Almeda, Calif.). Use of the paramagnetic microparticle detector significantly improved the sensitivity to detect Aβ oligomers with the 19.3/82E1 antibody pair.
Figure 9A:
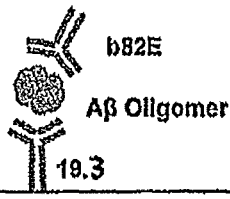
FIGS. 9A and 9B are graphic representations of the Aβ oligomer sandwich ELISA, i.e., the Pharmacodynamic (PD) Assay, and the Aβ oligomer/antibody sandwich ELISA, i.e., the Target Engagement Assay, respectively.

As an alternative, the 7305 detection antibody was replaced with 82E1, also coupled to a fluorescent tag, in the Aβ oligomer-selective sandwich ELISA (FIG. 9A) developed using the ERENNA Immunoassay System. Like 19.3, the 82E1 antibody has reported in ELISA formats to detect Aβ oligomers in AD brain (Xia, et al. (2009) Arch. Neurol. 66:190-199). As shown in Table 16, this assay eliminated the non-specific signal in both the neat and Aβ oligomer-depleted rhesus CSF, further suggesting that the 7305 antibody had been the source of the non-specific signal. Without wishing to be bound by any theory, the high background signal observed for the 19.3/7305 antibody pair was believed to be due to CSF fibrinogen binding to the MP beads, which was not observed for the 19.3/82E1 antibody pair. This alternative assay generated a LoD of the Aβ oligomer standards at 0.04 pg/mL, a LLoRQ at 0.42 pg/mL and 5000-fold selectivity of the assay for Aβ oligomers over Aβ 40 monomer (FIG. 8). On the basis of these findings, this assay format was selected for further characterization.

TABLE 16

| Parameter | 19.3/7305 Antibody Pair | 19.3/82E1 Antibody Pair |
|---|---|---|
| Slope detected events (pM) | 1,200 | 4,000 |
| Background | 70 | 100 |
| LoD (pM) | 0.01 | 0.01 |
| LLoRQ (pM) | 0.16-0.49 | 0.12 |
| Aβ40 monomer Cross Reactivity | 0.02% | 0.04% |
| Depleted Rhesus CSF (pM) | 80 | <0.12 |
| Non-Depleted Rhesus CSF (pM) | 200 | 0.35 |

Example 12

Pharmacodynamic (PD) Assay

Using the findings above, a selective Aβ oligomer sandwich ELISA was developed, using the 19.3 and 82E1 antibody pair, to detect and measure the levels of Aβ oligomers in a CSF sample. This assay will heretofore be called the pharmacodynamic (PD) assay for its use to assess changes in the analyte, i.e., Aβ oligomer, levels following treatment to inhibit production, increase clearance, or otherwise modify Aβ oligomer levels (FIG. 9S). The PD assay can also be used to differentiate AD from non-AD patients, i.e., diagnostic, to monitor the progression of the disease, i.e., prognostic, or to monitor the therapeutic potential of a disease-modifying treatment to change Aβ oligomer concentrations.

Figure 9B:
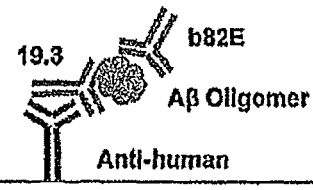

The PD assay, as described in the previous Example with reference to FIG. 9B, placed the 19.3 antibody coupled to a paramagnetic micro-particle (MP) bead (MP bead/19.3) into a well on an ELISA plate. To the well was added either a human CSF or an Aβ oligomer standard (in a dilution series added to a Tris buffer and bovine serum albumin). Any Aβ oligomer present in the well was bound by the 19.3/MP bead and the excess solution was washed away. Fluorescent-labeled 82E1, as the detection antibody, within an assay buffer (Tris buffer with 1% TRITON X-100, d-desthiobiotin, BSA), was added to the washed MP bead/19.3/Aβ oligomer complex and incubated, to bind the Aβ oligomer complex. The resulting MP bead/19.3/Aβ oligomer/82E1 complex was washed with an elution buffer and the fluorescent-labeled 82E1 antibody was eluted with any unbound antibody. Detection with the paramagnetic micro-particle detector, such as the ERENNA instrument, in which the solution flows by and is excited by a laser, allows the detection of single molecules (fluorescent tag emits photons of a specific light wavelength) to generate and measure a fluorescent signal, equivalent to the molecules detected, i.e., Aβ oligomer. A standard curve of Aβ oligomers, as measured with the ERENNA instrument, as compared to Aβ monomers is shown in FIG. 8.

Example 13

Aβ Oligomers in Human CSF

Figure 10A:
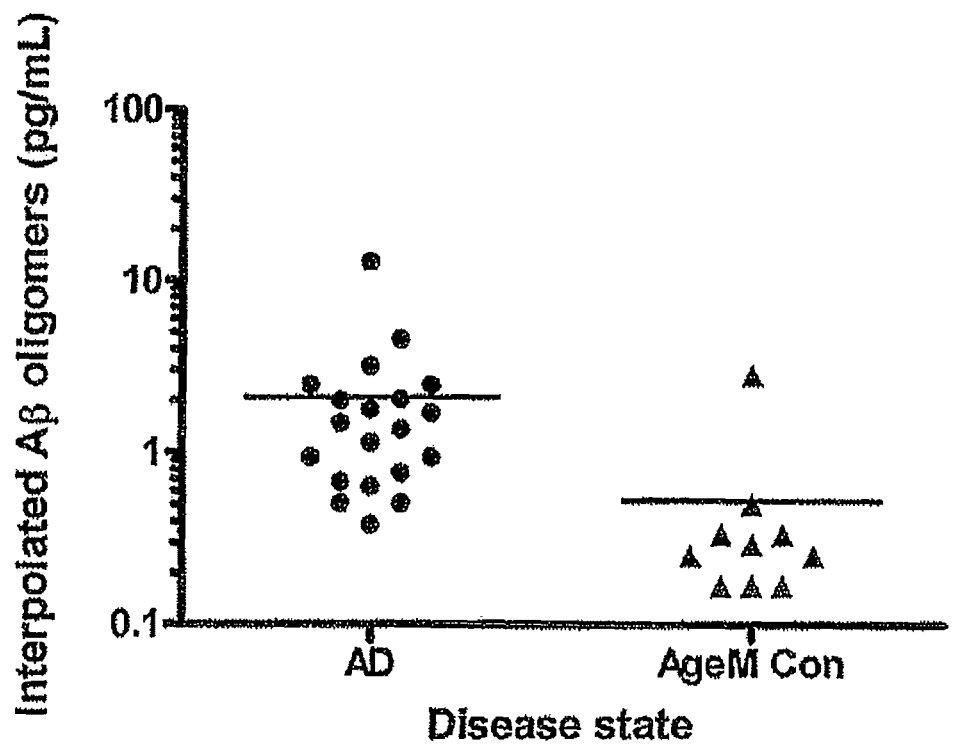
FIGS. 10A and 10B are graphic representations of the levels of Aβ oligomers detected in human cerebrospinal fluid (CSF) samples.
Figure 10B:
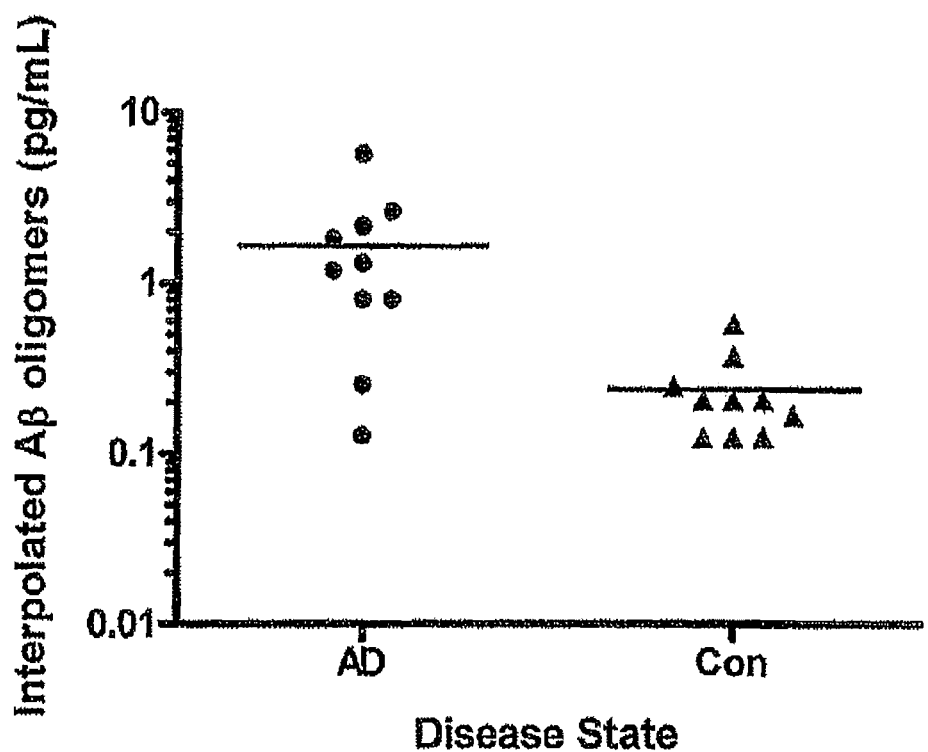
Figure 11A:
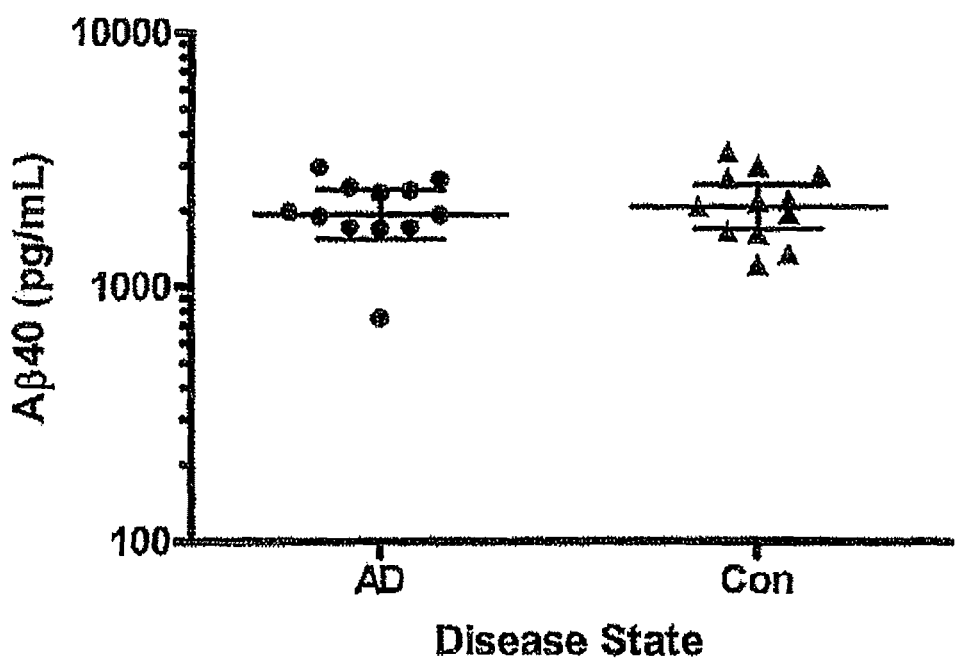
FIGS. 11A and 11B are graphic representations of Aβ monomer levels in the CSF of either clinically confirmed AD or young control, i.e., non-AD, patients, with a corresponding decrease in the levels of Aβ1-42 monomer and unchanged levels of Aβ1-40 monomer in the AD samples. This is representative of the general pattern observed for AD patients and confirmed the disease state of the samples evaluated in FIG. 10B.
Figure 11B:
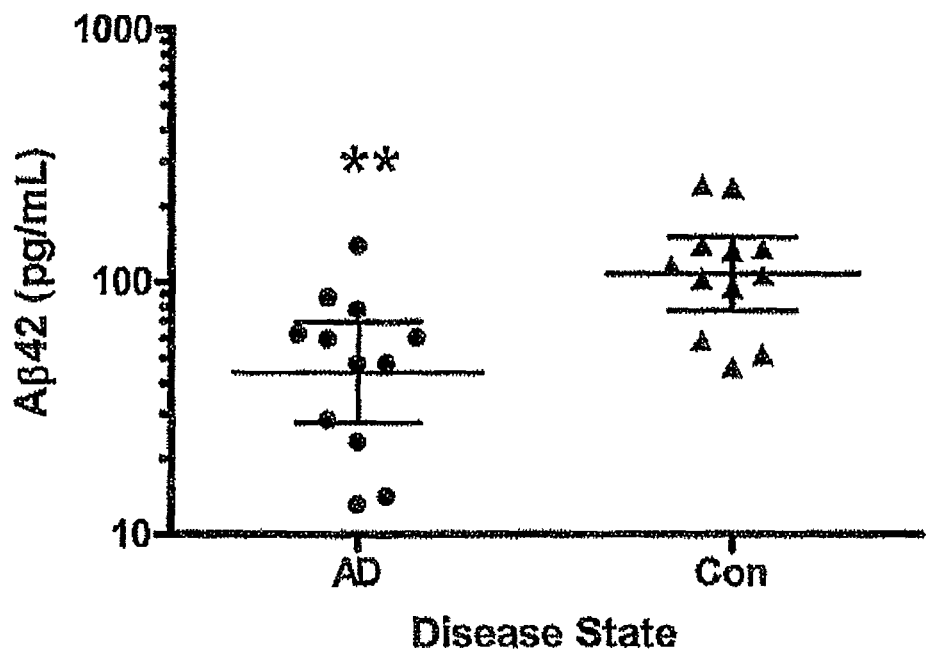

The 19.3×82E1 Aβ oligomer-selective sandwich ELISA of the previous Example was used to measure endogenous levels of Aβ oligomers in human CSF samples (FIGS. 10A and 10B). In two separate sample cohorts, the fluorescent signal, generated by the presence of Aβ oligomers, was significantly elevated in AD (clinically diagnosed using a MMSE score below 25 as probable AD) CSF as compared to either young or healthy age matched controls. The absolute levels of Aβ oligomers observed were 2.1±0.61 pg/mL in AD (n=20) and 0.53±0.26 pg/mL in age-matched control (n=10) in CSF samples from Precision Medicine (Solana Beach, Calif.) with a t-test, two way Mann-Whitney score of p<0.0004 (FIG. 10A). The absolute levels of Aβ oligomers observed were 1.66±0.5 pg/mL in AD (n=10) and 0.24±0.05 pg/mL in control (n=10) in CSF samples from Bioreclamation (Hicksville, N.Y.), with a t-test, two way Mann-Whitney score of p<0.0021 (FIG. 10B). Combining the two cohorts, 90% of the diagnosed AD CSF samples were above the LLoRQ of 0.42 pg/mL, while only 20% of the age-matched control or 10% of the young controls were above this limit. All values were above the LoD of 0.04 pg/mL. Aβ40 and Aβ42 monomer levels were measured in the CSF samples obtained from Bioreclamation (FIGS. 11A and 11B, respectively) and were comparable between the AD and control CSF for Aβ1-40 (FIG. 11A), while they were significantly reduced in the AD samples for Aβ1-42 (FIG. 11B). This has been previously reported as a feature of AD CSF (De Meyer, et al. (2010) *Arch. Neurol.* 67:949-956; Jack, et al. (2010) *Lancet Neural.* 9:119-128) and confirmed the correct diagnosis of these samples.

Without wishing to be bound to any theory, it is believed that the lower levels of Aβ1-42 in the AD CSF samples is due to retention of Aβ1-42 in the amyloid deposits of the AD brain. The ability to specifically detect and quantify these observed differences suggests that these biomarkers can be used as a diagnostic and prognostic measure for AD.

Figure 12:
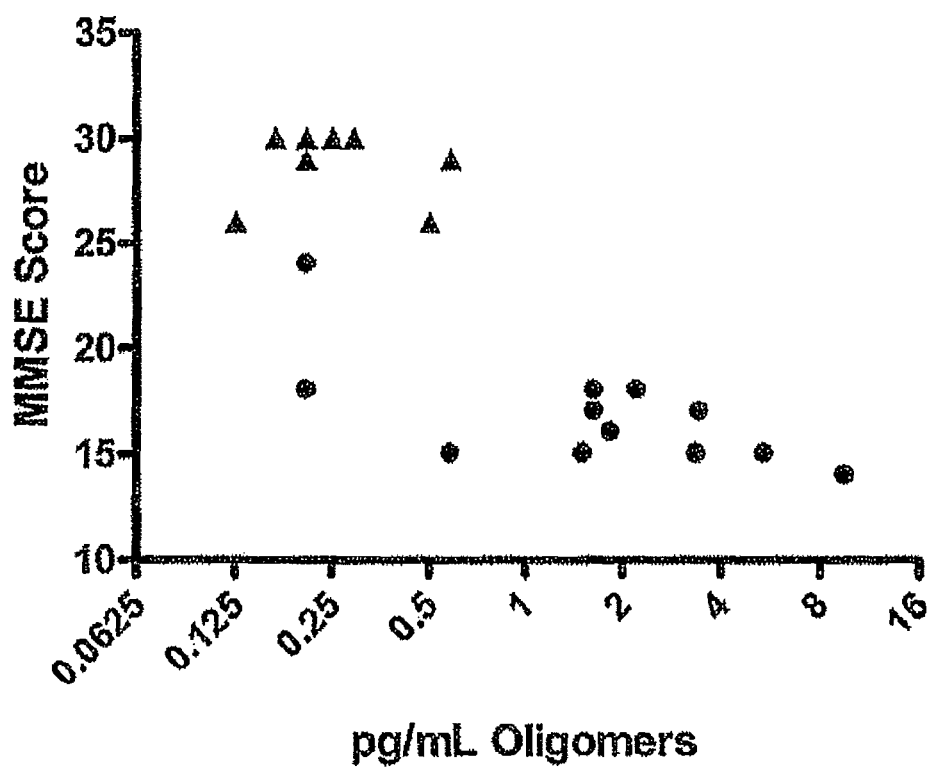
FIG. 12 is a graphic representation of the correlation between Mini-Mental State Exam (MMSE) scores, as a measure of cognitive performance, and levels of Aβ oligomer measured using the assay described herein. All patients depicted in FIG. 10B were included in this correlation. The correlation at −0.7445 pg/mL of Aβ oligomers was significant with p≤0.0001.

For a diagnostic assay, the signal, i.e., the level of Aβ oligomers, detected from the assay herein would typically be greater than three-fold higher for an AD patient (to a level >0.5 pg/mL) as compared to the signal observed for non-AD patients. This is consistent with the data, shown in both FIG. 10A, in which the levels of Aβ oligomers in the AD CSF compared to age-matched controls were four-fold higher, and in FIG. 10B, wherein levels of Aβ oligomers in AD CSF was eight-fold higher. This data also support the use of the Aβ oligomer assay herein to identify patients at early stages of disease (i.e., a prognostic assay). Age is the biggest risk factor for the development of AD and the differences observed between AD and age-matched controls were smaller than between AD and young controls. Similarly, for a prognostic Aβ oligomer assay, patients having a MMSE of below 25 would have a detected Aβ oligomer signal of >0.5 pg/ml, (four- to eight-fold higher than patients with MMSE above 25/normal) as compared to the signal detected for Aβ1-42 monomer, which is approximately two-fold lower in the AD CSF compared to controls. Using an MMSE score of 25 as a cutoff (Mungas (1991) *Geriatrics* 46(7): 4-58), wherein an MMSE score above 25 is considered "normal healthy" and below is considered as either mildly cognitively impaired, or as having AD, it would be expected that an Aβ oligomer level of ≥0.5 pg/mL is indicative of a patient with an MMSE score below 25 (FIG. 12).

Example 14

Target Engagement (TE) Assay

Using the findings above, a TE assay was developed to measure Aβ oligomers bound in vivo to a therapeutic (capture) antibody. As such, the TE assay can be used to measure levels of Aβ oligomers bound to a therapeutic antibody to confirm engagement of the Aβ oligomer by the therapeutic. Without wishing to be bound by any theory, it is believed that the level of Aβ oligomers bound to a therapeutic anti-Aβ oligomer antibody will be lower in CSF samples from subjects who have been treated over time with said therapeutic. Levels of bound Aβ oligomers that increase or are unchanged post-administration would suggest that the therapeutic is not suitable for the treatment of AD. Alternatively, it may be the case that merely by sequestering the Aβ oligomers and binding them to the therapeutic antibody, a benefit may be obtained in acute performance, due to reduced interaction with neurons in the brain. However, this benefit may not be associated with a change in Aβ oligomers per se. The target engagement assay would assess, at a minimum, the ability of a therapeutic antibody to engage Aβ oligomers within the CSF.

Figure 13:
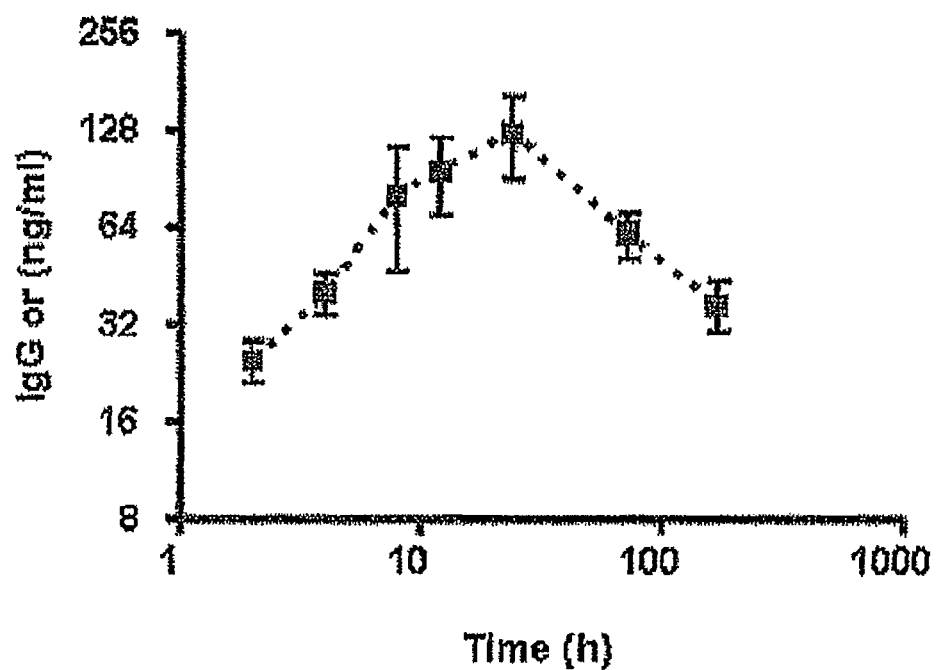
FIG. 13 is a graphical representation of the PK of anti-ADDL antibody 19.3 assessed in primate (three male rhesus monkeys) cerebrospinal fluid (CSF) using a cisterna magna ported rhesus model following administration of a bolus IV dose of 20 mg/kg. At about 24 hours post dose, antibody 19.3 was present in the CSF at 100 ng/mL.

In this assay an anti-human IgG2 antibody×82E1 antibody pair is used to detect and quantify levels of bound Aβ oligomers in a CSF sample from a patient treated with the anti-Aβ oligomer 19.3 (IgG2) antibody, i.e., a therapeutic antibody (FIG. 9B). To demonstrate the ability of Aβ oligomer-specific antibodies to engage Aβ oligomers in a human CSF matrix, 19.3/Aβ oligomers complexes were generated within human CSF by spiking the CSF with the anti-Aβ oligomer antibody 19.3 to levels believed to be present at 24 hours in rhesus monkey dosed IV with 20 m/k (100 ng/mL, FIG. 13). To this 19.3-spiked human CSF sample was added an escalating amount of Aβ oligomer standards, both matching endogenous Aβ oligomer concentrations (0.1-5.0 pg/mL) (FIGS. 10A and 10B) and also raising them significantly above normal ranges. The 19.3×Aβ oligomer complexes formed in human CSF were captured onto 96-well ELISA plates coated with either antibody to human kappa light chain or antibody to human IgG2 (both from Southern Biotech, Birmingnam, Ala.) at 0.5 μg per well in a sodium bicarbonate buffer overnight at 4° C. (BupH Carbonate-Bicarbonate Buffer pack, Thermo Fisher Scientific Inc, Waltham Mass.). Next day, the wells were washed with PBS-T and blocked overnight at 4° C. with 200 μL/well casein buffer in PBS with 0.1% TWEEN 20 added. The 19.3 antibody was spiked into a casein buffer (Thermo Fisher Scientific Inc, Waltham Mass.) or human CSF in microcentrifuge tubes (Axygen, Inc., Union City, Calif.). The Aβ oligomers were spiked at varying concentrations to give a standard curve, keeping the 19.3 levels constant. The samples were agitated at 4° C. for one hour to enable formation of the antibody (19.3)/Aβ oligomer complexes. One hundred μl sample/well was applied to either an anti-human IgG2 or an anti-human kappa-coated plate (n=3) and incubated overnight at 4° C. on a plate shaker. Next day, the plates were washed five times with PBS-T and Biotin-82E1 (IBL, Minneapolis, Minn.) was added at 100 μl/well, diluted 1:5000 in casein blocking buffer (Sigma-Aldrich Co., St. Louis, Mo.), 0.1% TWEEN 20 for one hour at room temperature. The plates were washed again with PBS-T, and Neutravidin-AP (ThermoFisher, Waltham, Mass.) was diluted 1:20000 in casein buffer, then added for 30 minutes at room temperature. Additional PBS-T washes were followed with TROPIX CDP star luminescence substrate (Applied Biosystems, Foster City, Calif.) applied for 30 minutes. Luminescence was quantified on an ENVISION plate reader (PerkinElmer, Waltham, Mass.).

Figure 14A:
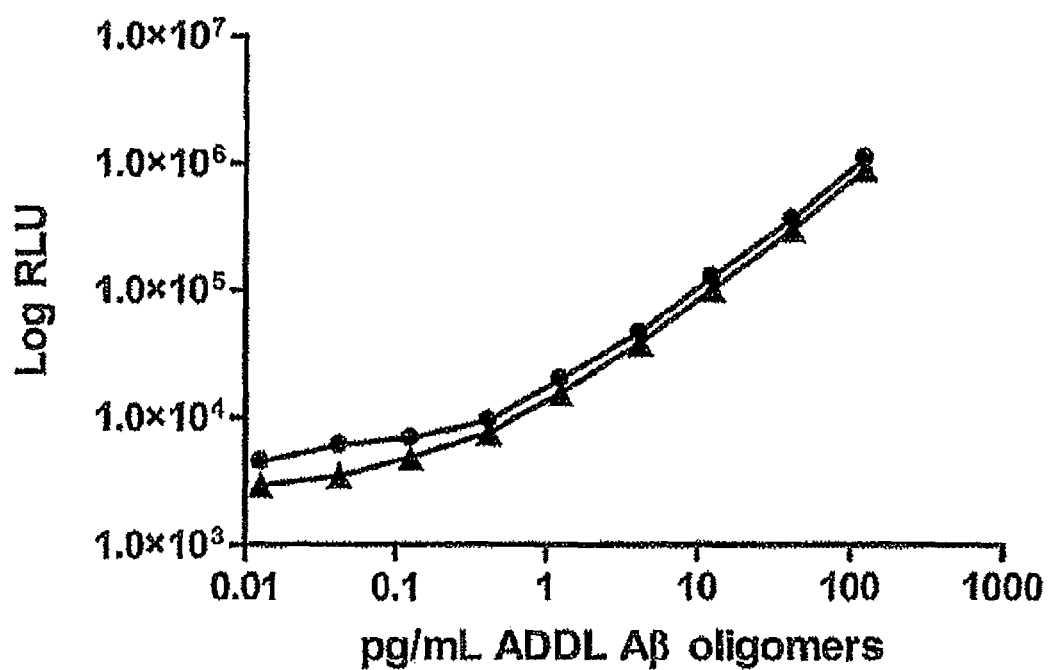
FIGS. 14A and 14B are graphical representations of the target engagement assay.
Figure 14B:
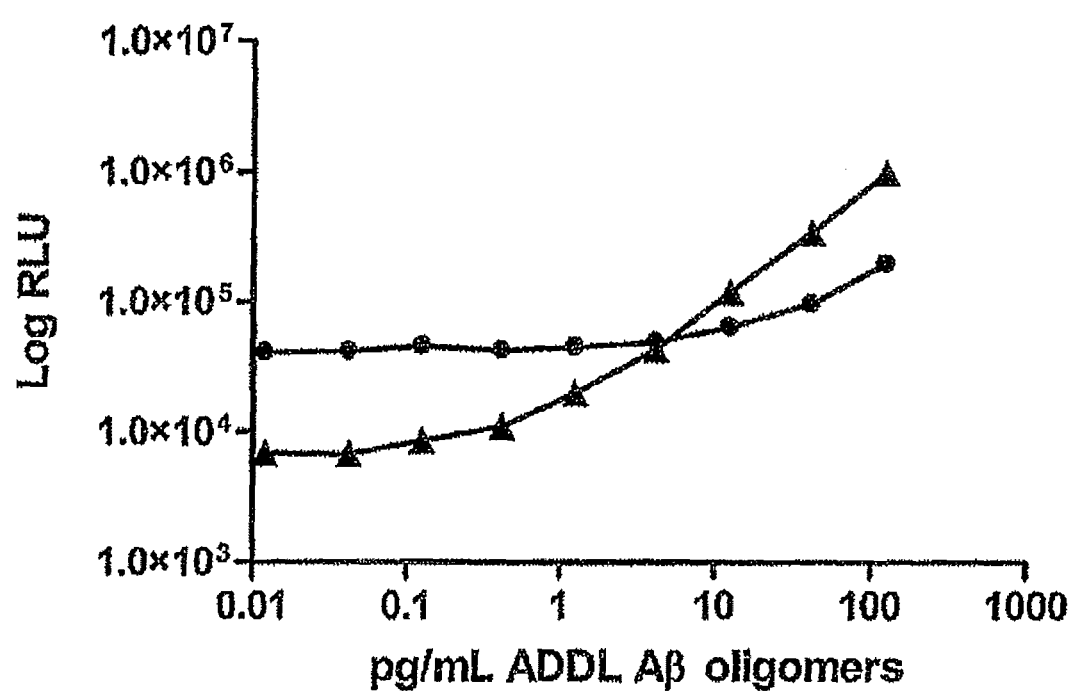

The anti-Aβ oligomer antibody 19.3 was sufficiently recognized by both anti-human kappa and anti-human IgG2 in buffer (FIGS. 14A and 14B, filled triangles), as the antibody contains both of these features. As shown in FIG. 14A (filled circle, CSF), the assay using anti-human IgG2 as the capture antibody and 82E1 as the detection antibody, to detect and measure the 19.3/Aβ oligomer complex, resulted in significantly better sensitivity in human CSF as compared to the assay using anti-human kappa as the capture antibody (filled circle, CSF, FIG. 14B). Both assays had equivalent sensitivity in casein buffer. Use of anti-human kappa to capture the 19.3/Aβ oligomer complex resulted in less sensitivity, to a LoD of 42 pg/mL Aβ oligomer bound to 100 ng/mL 19.3, perhaps due to higher background levels of IgG species with a kappa light chain in human CSF as compared to IgG2 species, which resulted in greater sensitivity for the assay format using an anti-IgG2. Following dosing of either human or experimental animals with 19.3 or a related IgG2 anti-Aβ oligomer antibody as a therapeutic antibody, one would expect the therapeutic antibody to be represented in the CSF at 0.1-0.2% of the dosed level (Thompson (2005) *Proteins of the Cerebrospinal Fluid*, Elsevier Academic Press, New York, N.Y.). The therapeutic antibody present in the CSF would be bound to available Aβ oligomers, the 19.3 (IgG2)/Aβ oligomer complexes would be captured with the anti-IgG2 capture antibody through the anti-human 19.3, IgG2, antibody, and the Aβ oligomer complexes would then be detected with 82E1. The sensitivity of this platform would likely improve using a paramagnetic microparticle detection system, such as the ERENNA immunoassay system (SINGULEX, Alameda, Calif.), utilized in the PD assay herein.

Over time, following therapeutic treatment with an anti-Aβ oligomer antibody, it is expected that the signal detected for the 19.3/Aβ-oligomer complexes would be reduced (as compared to pre-treatment levels). The amount of bound Aβ oligomer, whether as measured for these complexes acutely or after a period of therapeutic treatment, represents the proportion of the therapeutic antibody engaged with the target, i.e., Aβ oligomers, and could serve as a surrogate for the efficacy of the therapeutic antibody.

Example 15

Additional Antibody Characterization

A solution-based binding assay was used to determine the specificity and affinity of anti-ADDL antibodies to different amyloid beta peptide preparations (ADDL, fibril, Aβ-1-40, Aβ1-20). A quantitative ELISA was used that was capable of capturing the linear range of dose-response of monoclonal antibodies against ADDLs coated on NUNC plates. Based on this information, a fixed concentration of monoclonal antibody was selected that could give consistent OD signals in ELISA just above assay noise (OD450 nm reading around 0.2 to 0.5). Anti-ADDL antibody at this fixed concentration was then incubated with different amyloid beta peptide substrates (ADDL, fibril, Aβ1-40, Aβ1-20) in 20 point titrations in solution at room temperature overnight to reach equilibrium. The quantity of free anti-ADDL antibody within the mixture was determined the next day in a quantitative ELISA with one hour incubation on regular ELISA plates. The fraction of bound anti-ADDL antibody was calculated and the correlations of bound anti-ADDL antibody to titration of free ligand (substrates) were used to derive $K_D$, using the GRAFIT program (Erithacus Software, Surrey, UK). Thus, the substrate preference for each antibody to different amyloid beta peptide preparations was presented as the intrinsic affinity values ($K_D$).

Using this assay format, the interaction of the antibody and substrate was in the solution phase, thus, there was no constraint from any solid surface. Further, the interactions were allowed to reach equilibrium. Therefore, the interaction of anti-ADDL antibody and substrate occurred at limiting concentrations of both components with no concerns for precipitation of anti-ADDL antibody or additional amyloid beta peptide oligomerization due to high experimental concentration. Moreover, the assay readout was independent of antigen in the solution; thus, any heterology of amyloid beta in different peptide preparations (e.g., ADDL or fibril) would not interfere with data interpretation and mathematical modeling. The assay sensitivity was limited to ELISA assay detection limits, which allowed this assay to evaluate monoclonal antibodies with $K_D$ values in the nanomolar range.

The quantities of free anti-ADDL antibody were determined by a standard curve and plotted against titrations of different substrates. The quantities of bound anti-ADDL antibody with different substrates were plotted and the information was used in GRAFIT for curve fitting with appropriate mathematic models. The summary of $K_D$, expressed in nM ranges, for the panel of anti-ADDL monoclonal antibodies is presented in Table 17.

TABLE 17

| Antibody* | ADDL $K_D$ | ADDL SE | Fibril $K_D$ | Fibril SE | Aβ1-40 $K_D$ | Aβ1-40 SE | Aβ1-20 $K_D$ | Aβ1-20 SE |
|---|---|---|---|---|---|---|---|---|
| 20C2 | 0.92 | 0.09 | 3.62 | 0.47 | 30.48 | 5.05 | *71.35* | *24.41* |
| 2A10 | 2.29 | 0.25 | 6.72 | 0.99 | 14.69 | 2.64 | 22.40 | 2.43 |
| 2B4 | 2.09 | 0.24 | 10.50 | 1.26 | 27.57 | 4.88 | *1.63* | *0.26* |
| 2D6 | 5.05 | 0.52 | 14.41 | 2.40 | *25.66* | *5.84* | *30.17* | *7.07* |
| 5F10 | 11.90 | 1.63 | *28.95* | *5.78* | *23.54* | *6.21* | *6.10* | *4.39* |
| 4E2 | 4.26 | 0.42 | 9.40 | 1.60 | 20.24 | 2.07 | 28.40 | 3.23 |
| 4C2 | 8.08 | 1.03 | 19.17 | 3.69 | 21.89 | 4.14 | 28.40 | 3.23 |
| 1F4 | 9.24 | 0.84 | 12.52 | 1.66 | IC | IC | IC | IC |
| 1F6 | N/T | N/T | N/T | N/T | N/T | N/T | N/T | N/T |
| 2E12 | IC | IC | IC | IC | IC | IC | IC | IC |
| WO-2 | 0.57 | 0.042 | 1.15 | 0.12 | 6.15 | 0.62 | *19.26* | *3.53* |

*All antibodies were IgG.
Values listed in italic are high SE and poor fitting.
IC: inconclusive data.
N/T: not tested.

What is claimed is:

1. A kit for detecting oligomers of amyloid beta comprising:
   (a) a capture antibody that has an affinity for amyloid beta 1-42 oligomers compared to amyloid beta 1-40 monomers in a competitive binding assay of at least 500:1 and has:
   a light chain variable region comprising,
     (i) a CDR1 having the sequence Arg-Ser-Ser-Gln-Ser-Ile-Val-His-Ser-Xaa$_1$-Gly-Xaa$_2$-Thr-Tyr-Leu-Glu (SEQ ID NO:1), wherein Xaa$_1$ is Asn, Ser, Thr, Ala, Asp or Glu and Xaa$_2$ is Asn, His, Gln, Ser, Thr, Ala, or Asp,
     (ii) a CDR2 having the sequence Lys-Ala-Ser-Xaa$_1$-Arg-Phe-Ser (SEQ ID NO:2), wherein Xaa$_1$ is Asn, Gln, Ser, Thr, or Ala, and
     (iii) a CDR3 having the sequence Phe-Gln-Gly-Ser-Xaa$_1$-Xaa$_2$-Xaa$_3$-Xaa$_4$-Xaa$_5$ (SEQ ID NO:3), wherein Xaa$_1$ is Arg, Lys or Tyr, Xaa$_2$ is Val or Ala, Xaa$_3$ is Pro or His, Xaa$_4$ is Ala, Pro, or Val, and Xaa$_5$ is Ser, Gly, Arg or Phe; and
   a heavy chain variable region comprising,
     (i) a CDR1 of SEQ ID NO:4,
     (ii) a CDR2 of SEQ ID NO:5, and
     (iii) a CDR3 of SEQ ID NO:6; or
   a light chain variable region comprising,
     (i) a CDR1 having the sequence Arg-Ser-Ser-Gln-Ser-Ile-Val-His-Ser-Xaa$_1$-Gly-Xaa$_2$-Thr-Tyr-Leu-Glu (SEQ ID NO:1), wherein Xaa$_1$ is Ser, Thr, Ala, Asp or Glu and Xaa$_2$ is Asn, His, Gln, Ser, Thr, Ala, or Asp,
     (ii) a CDR2 having the sequence Lys-Ala-Ser-Xaa$_1$-Arg-Phe-Ser (SEQ ID NO:2), wherein Xaa$_1$ is Asn, Gln, Ser, Thr, or Ala, and
     (iii) a CDR3 of SEQ ID NO:16; and
   a heavy chain variable region comprising,
     (i) a CDR1 of SEQ ID NO:4,
     (ii) a CDR2 of SEQ ID NO:5, and
     (iii) a CDR3 of SEQ ID NO:6; and
   (b) a detection antibody that recognizes an N-terminal linear epitope of amyloid beta 1-42 peptide.

2. The kit of claim 1, wherein the affinity of the capture antibody for amyloid beta 1-42 oligomers compared to amyloid beta 1-42 monomers in a sandwich ELISA assay is at least 500:1.

3. The kit of claim 1, wherein the affinity of the capture antibody for amyloid beta 1-42 oligomers compared to amyloid beta 1-42 monomers in a sandwich ELISA assay is at least 1000:1.

4. The kit of claim 1, wherein the level of detection of amyloid beta 1-42 oligomers by said kit is less than 5 pg/mL.

5. The kit of claim 1, wherein the level of detection of amyloid beta 1-42 oligomers by said kit is less than 3 pg/mL.

6. The kit of claim 1, wherein the detection antibody is 6E10, BAM-10, W0-2, 26D6, 2A10, 2B4, 4C2, 4E2, 2H4, 20C2, 2D6, 5F10, 1F4, 1F6, 2E12, 3B3 or 82E1.

7. The kit of claim 1, wherein the detection antibody further comprises a label.

8. The kit of claim 1, further comprising a means for concentrating an antibody-antigen complex.

9. An isolated antibody, or antigen binding fragment thereof, that binds amyloid β-derived diffusible ligands, has an affinity for amyloid beta 1-42 oligomers compared to amyloid beta 1-40 monomers in a competitive binding assay of at least 500:1, and has:
   (a) a light chain variable region comprising,
     (i) a CDR1 having the sequence Arg-Ser-Ser-Gln-Ser-Ile-Val-His-Ser-Xaa$_1$-Gly-Xaa$_2$-Thr-Tyr-Leu-Glu (SEQ ID NO:1), wherein Xaa$_1$ is Ser, Thr, Ala, Asp or Glu and Xaa$_2$ is Asn, His, Gln, Ser, Thr, Ala, or Asp,
     (ii) a CDR2 of SEQ ID NO:15, and
     (iii) a CDR3 of SEQ ID NO:16; and
   (b) a heavy chain variable region comprising,
     (i) a CDR1 of SEQ ID NO:4,
     (ii) a CDR2 of SEQ ID NO:5, and
     (iii) a CDR3 of SEQ ID NO:6.

10. The antibody of claim 9, wherein the CDR1 of the light chain variable region has the sequence Arg-Ser-Ser-Gln-Ser-Ile-Val-His-Ser-Xaa$_1$-Gly-Xaa$_2$-Thr-Tyr-Leu-Glu (SEQ ID NO:1), wherein Xaa$_1$ is Thr, Ala, Asp or Glu and Xaa$_2$ is Thr.

11. An isolated antibody, or antigen binding fragment thereof, that binds amyloid β-derived diffusible ligands, has an affinity for amyloid beta 1-42 oligomers compared to amyloid beta 1-40 monomers in a competitive binding assay of at least 500:1, and has:
   (a) a light chain variable region comprising,
     (i) a CDR1 of SEQ ID NO:14,
     (ii) a CDR2 having the sequence Lys-Ala-Ser-Xaa$_1$-Arg-Phe-Ser (SEQ ID NO:2), wherein Xaa$_1$ is Gln, Ser, Thr, or Ala, and
     (iii) a CDR3 of SEQ ID NO:16; and
   (b) a heavy chain variable region comprising,
     (i) a CDR1 of SEQ ID NO:4,
     (ii) a CDR2 of SEQ ID NO:5, and
     (iii) a CDR3 of SEQ ID NO:6.

12. The antibody of claim 11, wherein the CDR2 of the light chain variable region has the sequence Lys-Ala-Ser-Xaa$_1$-Arg-Phe-Ser (SEQ ID NO:2), wherein Xaa$_1$ is Thr.

13. An isolated antibody, or antigen binding fragment thereof, that binds amyloid β-derived diffusible ligands comprising:
- a light chain variable region comprising,
    - (i) a CDR1 having the sequence Arg-Ser-Ser-Gln-Ser-Ile-Val-His-Ser-Xaa$_1$-Gly-Xaa$_2$-Thr-Tyr-Leu-Glu (SEQ ID NO:1), wherein Xaa$_1$ is Ser, Thr, Ala, Asp or Glu and Xaa$_2$ is Asn, His, Gln, Ser, Thr, Ala, or Asp,
    - (ii) a CDR2 having the sequence Lys-Ala-Ser-Xaa$_1$-Arg-Phe-Ser (SEQ ID NO:2), wherein Xaa$_1$ is Asn, Gln, Ser, Thr, or Ala, and
    - (iii) a CDR3 having the sequence Phe-Gln-Gly-Ser-Xaa$_1$-Xaa$_2$-Xaa$_3$-Xaa$_4$-Xaa$_5$ (SEQ ID NO:3), wherein Xaa$_1$ is Arg, Lys or Tyr, Xaa$_2$ is Val, Ala or Leu, Xaa$_3$ is Pro, His or Gly, Xaa$_4$ is Ala, Pro, or Val, and Xaa$_5$ is Ser, Gly, Arg or Phe; and
- a heavy chain variable region comprising,
    - (i) a CDR1 of SEQ ID NO:4,
    - (ii) a CDR2 of SEQ ID NO:5, and
    - (iii) a CDR3 of SEQ ID NO:6.

\* \* \* \* \*

SEQUENCE LISTING

```
<160> NUMBER OF SEQ ID NOS: 58

<210> SEQ ID NO 1
<211> LENGTH: 16
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: Xaa denotes N, S, T, A, D or E;  or Xaa denotes
      T, A, D, or E.
<220> FEATURE:
<221> NAME/KEY: MISC_FEATURE
<222> LOCATION: (12)..(12)
<223> OTHER INFORMATION: Xaa denotes N, H, Q, S, T, A or D; or Xaa
      denotes T.

<400> SEQUENCE: 1

Arg Ser Ser Gln Ser Ile Val His Ser Xaa Gly Xaa Thr Tyr Leu Glu
1               5                   10                  15

<210> SEQ ID NO 2
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa denotes N, G, S, T or A; or Xaa denotes T.

<400> SEQUENCE: 2

Lys Ala Ser Xaa Arg Phe Ser
1               5

<210> SEQ ID NO 3
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa denotes R, K or Y.
<220> FEATURE:
<221> NAME/KEY: MISC_FEATURE
<222> LOCATION: (6)..(6)
<223> OTHER INFORMATION: Xaa denotes V, A or L.
<220> FEATURE:
<221> NAME/KEY: MISC_FEATURE
<222> LOCATION: (7)..(7)
<223> OTHER INFORMATION: Xaa denotes P, H or G.
<220> FEATURE:
```

```
<221> NAME/KEY: MISC_FEATURE
<222> LOCATION: (8)..(8)
<223> OTHER INFORMATION: Xaa denotes A, P or V.
<220> FEATURE:
<221> NAME/KEY: MISC_FEATURE
<222> LOCATION: (9)..(9)
<223> OTHER INFORMATION: Xaa denotes S, G or F.

<400> SEQUENCE: 3

Phe Gln Gly Ser Xaa Xaa Xaa Xaa Xaa
1               5

<210> SEQ ID NO 4
<211> LENGTH: 10
<212> TYPE: PRT
<213> ORGANISM: Artificial sequence
<220> FEATURE:
<223> OTHER INFORMATION: Synthetic peptide

<400> SEQUENCE: 4

Gly Phe Thr Phe Ser Ser Phe Gly Met His
1               5                   10

<210> SEQ ID NO 5
<211> LENGTH: 17
<212> TYPE: PRT
<213> ORGANISM: Artificial sequence
<220> FEATURE:
<223> OTHER INFORMATION: Synthetic peptide

<400> SEQUENCE: 5

Tyr Ile Ser Arg Gly Ser Ser Thr Ile Tyr Tyr Ala Asp Thr Val Lys
1               5                   10                  15

Gly

<210> SEQ ID NO 6
<211> LENGTH: 8
<212> TYPE: PRT
<213> ORGANISM: Artificial sequence
<220> FEATURE:
<223> OTHER INFORMATION: Synthetic peptide

<400> SEQUENCE: 6

Gly Ile Thr Thr Ala Leu Asp Tyr
1               5

<210> SEQ ID NO 7
<211> LENGTH: 42
<212> TYPE: PRT
<213> ORGANISM: Homo sapiens

<400> SEQUENCE: 7

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 8
<211> LENGTH: 7
<212> TYPE: PRT
<213> ORGANISM: Artificial sequence
<220> FEATURE:
<223> OTHER INFORMATION: Synthetic peptide
```

```
<400> SEQUENCE: 8

Arg His Asp Ser Gly Tyr Glu
1               5

<210> SEQ ID NO 9
<211> LENGTH: 6
<212> TYPE: PRT
<213> ORGANISM: Artificial sequence
<220> FEATURE:
<223> OTHER INFORMATION: Synthetic peptide

<400> SEQUENCE: 9

Glu Phe Arg His Asp Ser
1               5

<210> SEQ ID NO 10
<211> LENGTH: 11
<212> TYPE: PRT
<213> ORGANISM: Artificial sequence
<220> FEATURE:
<223> OTHER INFORMATION: Synthetic peptide

<400> SEQUENCE: 10

Glu Val His His Gln Lys Leu Val Phe Phe Ala
1               5                   10

<210> SEQ ID NO 11
<211> LENGTH: 8
<212> TYPE: PRT
<213> ORGANISM: Artificial sequence
<220> FEATURE:
<223> OTHER INFORMATION: Synthetic peptide

<400> SEQUENCE: 11

Asp Ala Glu Phe Arg His Asp Ser
1               5

<210> SEQ ID NO 12
<211> LENGTH: 8
<212> TYPE: PRT
<213> ORGANISM: Artificial sequence
<220> FEATURE:
<223> OTHER INFORMATION: Synthetic peptide

<400> SEQUENCE: 12

Glu Phe Arg His Asp Ser Gly Tyr
1               5

<210> SEQ ID NO 13
<211> LENGTH: 5
<212> TYPE: PRT
<213> ORGANISM: Artificial sequence
<220> FEATURE:
<223> OTHER INFORMATION: Synthetic peptide

<400> SEQUENCE: 13

Asp Ala Glu Phe Arg
1               5

<210> SEQ ID NO 14
<211> LENGTH: 16
<212> TYPE: PRT
<213> ORGANISM: Artificial sequence
<220> FEATURE:
<223> OTHER INFORMATION: Synthetic peptide

<400> SEQUENCE: 14
```

Arg Ser Ser Gln Ser Ile Val His Ser Asn Gly Asn Thr Tyr Leu Glu
1               5                   10                  15

<210> SEQ ID NO 15
<211> LENGTH: 7
<212> TYPE: PRT
<213> ORGANISM: Artificial sequence
<220> FEATURE:
<223> OTHER INFORMATION: Synthetic peptide

<400> SEQUENCE: 15

Lys Ala Ser Asn Arg Phe Ser
1               5

<210> SEQ ID NO 16
<211> LENGTH: 9
<212> TYPE: PRT
<213> ORGANISM: Artificial sequence
<220> FEATURE:
<223> OTHER INFORMATION: Synthetic peptide

<400> SEQUENCE: 16

Phe Gln Gly Ser Arg Leu Gly Pro Ser
1               5

<210> SEQ ID NO 17
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 17
tatggcttct agagatgtgg tgatg                                         25

<210> SEQ ID NO 18
<211> LENGTH: 82
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (62)..(63)
<223> OTHER INFORMATION: n is a, c, g, or t
<220> FEATURE:
<221> NAME/KEY: misc_feature
<222> LOCATION: (65)..(66)
<223> OTHER INFORMATION: n is a, c, g, or t
<220> FEATURE:
<221> NAME/KEY: misc_feature
<222> LOCATION: (68)..(69)
<223> OTHER INFORMATION: n is a, c, g, or t
<220> FEATURE:
<221> NAME/KEY: misc_feature
<222> LOCATION: (71)..(72)
<223> OTHER INFORMATION: n is a, c, g, or t

<400> SEQUENCE: 18
tgcagccacc gtacgcttga tctccagctt ggtgccctgg ccaaaggtgg ggggcacmnn   60
mnnmnnmnnm nngcagtagt ag                                            82

<210> SEQ ID NO 19
<211> LENGTH: 70
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t

<400> SEQUENCE: 19
tgcagccacc gtacgcttga tctccagctt ggtgccctgg ccaaamnmn nmnnmnnmnn        60 gctgccctgg                                                             70

<210> SEQ ID NO 20
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 20
aggcggccct cgaggaggtg cagc                                             24

<210> SEQ ID NO 21
<211> LENGTH: 83
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (60)..(61)
<223> OTHER INFORMATION: n is a, c, g, or t
<220> FEATURE:
<221> NAME/KEY: misc_feature
<222> LOCATION: (63)..(64)
<223> OTHER INFORMATION: n is a, c, g, or t
<220> FEATURE:
<221> NAME/KEY: misc_feature
<222> LOCATION: (66)..(67)
<223> OTHER INFORMATION: n is a, c, g, or t
<220> FEATURE:
<221> NAME/KEY: misc_feature
<222> LOCATION: (69)..(70)
<223> OTHER INFORMATION: n is a, c, g, or t
<220> FEATURE:
<221> NAME/KEY: misc_feature
<222> LOCATION: (72)..(73)
<223> OTHER INFORMATION: n is a, c, g, or t

```
<400> SEQUENCE: 21
agaccgatgg gcccttggtg gaggcgctgg acacggtcac cagggtgccc tggccccamn      60
nmnnmnnmnn mnnggtgatg ccc                                              83

<210> SEQ ID NO 22
<211> LENGTH: 92
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (69)..(70)
<223> OTHER INFORMATION: n is a, c, g, or t
<220> FEATURE:
<221> NAME/KEY: misc_feature
<222> LOCATION: (72)..(73)
<223> OTHER INFORMATION: n is a, c, g, or t
<220> FEATURE:
<221> NAME/KEY: misc_feature
<222> LOCATION: (75)..(76)
<223> OTHER INFORMATION: n is a, c, g, or t
<220> FEATURE:
<221> NAME/KEY: misc_feature
<222> LOCATION: (78)..(79)
<223> OTHER INFORMATION: n is a, c, g, or t
<220> FEATURE:
<221> NAME/KEY: misc_feature
<222> LOCATION: (81)..(82)
<223> OTHER INFORMATION: n is a, c, g, or t

<400> SEQUENCE: 22
agaccgatgg gcccttggtg gaggcgctgg acacggtcac cagggtgccc tggccccagt      60
agtccagmnn mnnmnnmnnm nnccgggcac ag                                    92

<210> SEQ ID NO 23
<211> LENGTH: 9
<212> TYPE: PRT
<213> ORGANISM: Artificial sequence
<220> FEATURE:
<223> OTHER INFORMATION: Synthetic peptide

<400> SEQUENCE: 23

Phe Gln Gly Ser His Val Pro Pro Thr
1               5

<210> SEQ ID NO 24
<211> LENGTH: 9
<212> TYPE: PRT
<213> ORGANISM: Artificial sequence
<220> FEATURE:
<223> OTHER INFORMATION: Synthetic peptide

<400> SEQUENCE: 24

Phe Gln Gly Ser Arg Val Pro Ala Ser
1               5

<210> SEQ ID NO 25
<211> LENGTH: 9
<212> TYPE: PRT
<213> ORGANISM: Artificial sequence
<220> FEATURE:
<223> OTHER INFORMATION: Synthetic peptide
```

```
-continued

<400> SEQUENCE: 25

Phe Gln Gly Ser Arg Val Pro Pro Gly
1               5

<210> SEQ ID NO 26
<211> LENGTH: 9
<212> TYPE: PRT
<213> ORGANISM: Artificial sequence
<220> FEATURE:
<223> OTHER INFORMATION: Synthetic peptide

<400> SEQUENCE: 26

Phe Gln Gly Ser Lys Ala His Pro Ser
1               5

<210> SEQ ID NO 27
<211> LENGTH: 9
<212> TYPE: PRT
<213> ORGANISM: Artificial sequence
<220> FEATURE:
<223> OTHER INFORMATION: Synthetic peptide

<400> SEQUENCE: 27

Phe Gln Gly Ser Tyr Ala Pro Pro Gly
1               5

<210> SEQ ID NO 28
<211> LENGTH: 9
<212> TYPE: PRT
<213> ORGANISM: Artificial sequence
<220> FEATURE:
<223> OTHER INFORMATION: Synthetic peptide

<400> SEQUENCE: 28

Phe Gln Gly Ser Arg Ala Pro Pro Phe
1               5

<210> SEQ ID NO 29
<211> LENGTH: 9
<212> TYPE: PRT
<213> ORGANISM: Artificial sequence
<220> FEATURE:
<223> OTHER INFORMATION: Synthetic peptide

<400> SEQUENCE: 29

Phe Gln Gly Ser Arg Val Pro Val Arg
1               5

<210> SEQ ID NO 30
<211> LENGTH: 95
<212> TYPE: PRT
<213> ORGANISM: Artificial Sequence
<220> FEATURE:
<223> OTHER INFORMATION: Synthetic peptide

<400> SEQUENCE: 30

Pro Ala Ser Ile Ser Cys Arg Ser Ser Gln Ser Ile Val His Ser Asn
1               5                   10                  15

Gly Asn Thr Tyr Leu Glu Trp Tyr Leu Gln Lys Pro Gly Gln Ser Pro
            20                  25                  30

Gln Leu Leu Ile Tyr Lys Ala Ser Asn Arg Phe Ser Gly Val Pro Asp
        35                  40                  45

Arg Phe Ser Gly Ser Gly Ser Gly Thr Asp Phe Thr Leu Lys Ile Ser
    50                  55                  60
```

```
Arg Val Glu Ala Glu Asp Val Gly Val Tyr Tyr Cys Phe Gln Gly Ser
 65                  70                  75                  80

His Val Pro Pro Thr Phe Gly Gln Gly Thr Lys Leu Glu Ile Lys
                 85                  90                  95

<210> SEQ ID NO 31
<211> LENGTH: 95
<212> TYPE: PRT
<213> ORGANISM: Artificial sequence
<220> FEATURE:
<223> OTHER INFORMATION: Synthetic peptide

<400> SEQUENCE: 31

Pro Ala Ser Ile Ser Cys Arg Ser Ser Gln Ser Ile Val His Ser Asn
  1               5                  10                  15

Gly Asn Thr Tyr Leu Glu Trp Tyr Leu Gln Lys Pro Gly Gln Ser Pro
                 20                  25                  30

Gln Leu Leu Ile Tyr Lys Ala Ser Asn Arg Phe Ser Gly Val Pro Asp
             35                  40                  45

Arg Phe Ser Gly Ser Gly Ser Gly Thr Asp Phe Thr Leu Lys Ile Ser
 50                  55                  60

Arg Val Glu Ala Glu Asp Val Gly Val Tyr Tyr Cys Phe Gln Gly Ser
 65                  70                  75                  80

Arg Leu Gly Pro Ser Phe Gly Gln Gly Thr Lys Leu Glu Ile Lys
                 85                  90                  95

<210> SEQ ID NO 32
<211> LENGTH: 95
<212> TYPE: PRT
<213> ORGANISM: Artificial sequence
<220> FEATURE:
<223> OTHER INFORMATION: Synthetic peptide

<400> SEQUENCE: 32

Pro Ala Ser Ile Ser Cys Arg Ser Ser Gln Ser Ile Val His Ser Asn
  1               5                  10                  15

Gly Asn Thr Tyr Leu Glu Trp Tyr Leu Gln Lys Pro Gly Gln Ser Pro
                 20                  25                  30

Gln Leu Leu Ile Tyr Lys Ala Ser Asn Arg Phe Ser Gly Val Pro Asp
             35                  40                  45

Arg Phe Ser Gly Ser Gly Ser Gly Thr Asp Phe Thr Leu Lys Ile Ser
 50                  55                  60

Arg Val Glu Ala Glu Asp Val Gly Val Tyr Tyr Cys Phe Gln Gly Ser
 65                  70                  75                  80

Arg Val Pro Ala Ser Phe Gly Gln Gly Thr Lys Leu Glu Ile Lys
                 85                  90                  95

<210> SEQ ID NO 33
<211> LENGTH: 95
<212> TYPE: PRT
<213> ORGANISM: Artificial sequence
<220> FEATURE:
<223> OTHER INFORMATION: Synthetic peptide

<400> SEQUENCE: 33

Pro Ala Ser Ile Ser Cys Arg Ser Ser Gln Ser Ile Val His Ser Asn
  1               5                  10                  15

Gly Asn Thr Tyr Leu Glu Trp Tyr Leu Gln Lys Pro Gly Gln Ser Pro
                 20                  25                  30
```

Gln Leu Leu Ile Tyr Lys Ala Ser Asn Arg Phe Ser Gly Val Pro Asp
                35                  40                  45

Arg Phe Ser Gly Ser Gly Ser Gly Thr Asp Phe Thr Leu Lys Ile Ser
 50                  55                  60

Arg Val Glu Ala Glu Asp Val Gly Val Tyr Tyr Cys Phe Gln Gly Ser
 65                  70                  75                  80

Arg Val Pro Pro Gly Phe Gly Gln Gly Thr Lys Leu Glu Ile Lys
                 85                  90                  95

<210> SEQ ID NO 34
<211> LENGTH: 95
<212> TYPE: PRT
<213> ORGANISM: Artificial sequence
<220> FEATURE:
<223> OTHER INFORMATION: Synthetic peptide

<400> SEQUENCE: 34

Pro Ala Ser Ile Ser Cys Arg Ser Ser Gln Ser Ile Val His Ser Asn
 1               5                  10                  15

Gly Asn Thr Tyr Leu Glu Trp Tyr Leu Gln Lys Pro Gly Gln Ser Pro
                20                  25                  30

Gln Leu Leu Ile Tyr Lys Ala Ser Asn Arg Phe Ser Gly Val Pro Asp
                35                  40                  45

Arg Phe Ser Gly Ser Gly Ser Gly Thr Asp Phe Thr Leu Lys Ile Ser
 50                  55                  60

Arg Val Glu Ala Glu Asp Val Gly Val Tyr Tyr Cys Phe Gln Gly Ser
 65                  70                  75                  80

Lys Ala His Pro Ser Phe Gly Gln Gly Thr Lys Leu Glu Ile Lys
                 85                  90                  95

<210> SEQ ID NO 35
<211> LENGTH: 95
<212> TYPE: PRT
<213> ORGANISM: Artificial sequence
<220> FEATURE:
<223> OTHER INFORMATION: Synthetic peptide

<400> SEQUENCE: 35

Pro Ala Ser Ile Ser Cys Arg Ser Ser Gln Ser Ile Val His Ser Asn
 1               5                  10                  15

Gly Asn Thr Tyr Leu Glu Trp Tyr Leu Gln Lys Pro Gly Gln Ser Pro
                20                  25                  30

Gln Leu Leu Ile Tyr Lys Ala Ser Asn Arg Phe Ser Gly Val Pro Asp
                35                  40                  45

Arg Phe Ser Gly Ser Gly Ser Gly Thr Asp Phe Thr Leu Lys Ile Ser
 50                  55                  60

Arg Val Glu Ala Glu Asp Val Gly Val Tyr Tyr Cys Phe Gln Gly Ser
 65                  70                  75                  80

Tyr Ala Pro Pro Gly Phe Gly Gln Gly Thr Lys Leu Glu Ile Lys
                 85                  90                  95

<210> SEQ ID NO 36
<211> LENGTH: 95
<212> TYPE: PRT
<213> ORGANISM: Artificial sequence
<220> FEATURE:
<223> OTHER INFORMATION: Synthetic peptide

<400> SEQUENCE: 36

Pro Ala Ser Ile Ser Cys Arg Ser Ser Gln Ser Ile Val His Ser Asn

```
                1               5                  10                 15
Gly Asn Thr Tyr Leu Glu Trp Tyr Leu Gln Lys Pro Gly Gln Ser Pro
            20                  25                 30

Gln Leu Leu Ile Tyr Lys Ala Ser Asn Arg Phe Ser Gly Val Pro Asp
            35                  40                 45

Arg Phe Ser Gly Ser Gly Ser Gly Thr Asp Phe Thr Leu Lys Ile Ser
        50                  55                  60

Arg Val Glu Ala Glu Asp Val Gly Val Tyr Tyr Cys Phe Gln Gly Ser
65                  70                  75                  80

Arg Ala Pro Pro Phe Phe Gly Gln Gly Thr Lys Leu Glu Ile Lys
                85                  90                 95

<210> SEQ ID NO 37
<211> LENGTH: 95
<212> TYPE: PRT
<213> ORGANISM: Artificial sequence
<220> FEATURE:
<223> OTHER INFORMATION: Synthetic peptide

<400> SEQUENCE: 37

Pro Ala Ser Ile Ser Cys Arg Ser Ser Gln Ser Ile Val His Ser Asn
1               5                  10                 15

Gly Asn Thr Tyr Leu Glu Trp Tyr Leu Gln Lys Pro Gly Gln Ser Pro
            20                  25                 30

Gln Leu Leu Ile Tyr Lys Ala Ser Asn Arg Phe Ser Gly Val Pro Asp
            35                  40                 45

Arg Phe Ser Gly Ser Gly Ser Gly Thr Asp Phe Thr Leu Lys Ile Ser
        50                  55                  60

Arg Val Glu Ala Glu Asp Val Gly Val Tyr Tyr Cys Phe Gln Gly Ser
65                  70                  75                  80

Arg Val Pro Val Arg Phe Gly Gln Gly Thr Lys Leu Glu Ile Lys
                85                  90                 95

<210> SEQ ID NO 38
<211> LENGTH: 981
<212> TYPE: DNA
<213> ORGANISM: Artificial sequence
<220> FEATURE:
<223> OTHER INFORMATION: Synthetic polynucleotide

<400> SEQUENCE: 38
gcatccacca agggcccatc cgtcttcccc ctggcgccct gctccaggag cacctccgag      60
agcacagccg ccctgggctg cctggtcaag gactacttcc ccgaaccggt gacggtgtcc     120
tggaactctg gcgccctgac ctctggcgtg cacaccttcc ctgctgtgct gcaatcctct     180
ggcctgtact cctgtcctc tgtggtgaca gtgccatcct ccaacttcgg cacccagacc      240
tacacatgca atgtggacca caagccatcc aacaccaagg tggacaagac agtggagcgg     300
aagtgctgtg tggagtgccc cccatgccct gccccccctg tggctggccc atctgtgttc     360
ctgttccccc ccaagcccaa ggacaccctg atgatctccc ggacccctga ggtgacctgt     420
gtggtggtgg acgtgtccca tgaggaccct gaggtgcagt tcaactggta tgtggatggc     480
gtggaggtgc acaatgccaa gaccaagccc cgggaggagc agttcaactc cacccttcgg     540
gtggtgtctg tgctgacagt ggtgcaccag gactggctga atggcaagga gtacaagtgc     600
aaggtgtcca acaagggcct gcctgccccc atcgagaaga ccatctccaa gaccaagggc     660
cagccccggg agccccaggt gtacaccctg cccccatccc gggaggagat gaccaagaac     720
```

```
caggtgtccc tgacctgcct ggtgaagggc ttctacccat ccgacattgc tgtggagtgg    780
gagtccaatg ccagcctga gaacaactac aagaccaccc ccccatgct ggactctgat     840 ggctccttct tcctgtactc caagctgaca gtggacaagt cccggtggca gcagggcaat    900
gtgttctcct gctctgtgat gcatgaggcc ctgcacaacc actacaccca gaagtccctg    960
tccctgtccc ctggcaagtg a                                              981
```

<210> SEQ ID NO 39  
<211> LENGTH: 326  
<212> TYPE: PRT  
<213> ORGANISM: Artificial sequence  
<220> FEATURE:  
<223> OTHER INFORMATION: Synthetic polypeptide
<400> SEQUENCE: 39

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320
```

```
Ser Leu Ser Pro Gly Lys
                325

<210> SEQ ID NO 40
<211> LENGTH: 324
<212> TYPE: PRT
<213> ORGANISM: Artificial sequence
<220> FEATURE:
<223> OTHER INFORMATION: Synthetic polynucleotide

<400> SEQUENCE: 40

Cys Gly Thr Ala Cys Gly Gly Thr Gly Gly Cys Thr Gly Cys Ala Cys
1               5                   10                  15

Cys Ala Thr Cys Thr Gly Thr Cys Thr Thr Cys Ala Thr Cys Thr Thr
            20                  25                  30

Cys Cys Cys Gly Cys Cys Ala Thr Cys Thr Gly Ala Thr Gly Ala Gly
        35                  40                  45

Cys Ala Gly Thr Thr Gly Ala Ala Ala Thr Cys Thr Gly Gly Ala Ala
    50                  55                  60

Cys Thr Gly Cys Cys Thr Cys Thr Gly Thr Thr Gly Thr Gly Thr Gly
65                  70                  75                  80

Cys Cys Thr Gly Cys Thr Gly Ala Ala Thr Ala Ala Cys Thr Thr Cys
                85                  90                  95

Thr Ala Thr Cys Cys Cys Ala Gly Ala Gly Ala Gly Gly Cys Cys Ala
            100                 105                 110

Ala Ala Gly Thr Ala Cys Ala Gly Thr Gly Gly Ala Ala Gly Gly Thr
        115                 120                 125

Gly Gly Ala Thr Ala Ala Cys Gly Cys Cys Cys Thr Cys Cys Ala Ala
    130                 135                 140

Thr Cys Gly Gly Gly Thr Ala Ala Cys Thr Cys Cys Cys Ala Gly Gly
145                 150                 155                 160

Ala Gly Ala Gly Thr Gly Thr Cys Ala Cys Ala Gly Ala Gly Cys Ala
                165                 170                 175

Gly Gly Ala Cys Ala Gly Cys Ala Ala Gly Gly Ala Cys Ala Gly Cys
            180                 185                 190

Ala Cys Cys Thr Ala Cys Ala Gly Cys Cys Thr Cys Ala Gly Cys Ala
        195                 200                 205

Gly Cys Ala Cys Cys Cys Thr Gly Ala Cys Gly Cys Thr Gly Ala Gly
    210                 215                 220

Cys Ala Ala Ala Gly Cys Ala Gly Ala Cys Thr Ala Cys Gly Ala Gly
225                 230                 235                 240

Ala Ala Ala Cys Ala Cys Ala Ala Ala Gly Thr Cys Thr Ala Cys Gly
                245                 250                 255

Cys Cys Thr Gly Cys Gly Ala Ala Gly Thr Cys Ala Cys Cys Cys Ala
            260                 265                 270

Thr Cys Ala Gly Gly Gly Cys Cys Thr Gly Ala Gly Cys Thr Cys Gly
        275                 280                 285

Cys Cys Cys Gly Thr Cys Ala Cys Ala Ala Ala Gly Ala Gly Cys Thr
    290                 295                 300

Thr Cys Ala Ala Cys Ala Gly Gly Gly Gly Ala Gly Ala Gly Thr Gly
305                 310                 315                 320

Thr Thr Ala Gly
```

<210> SEQ ID NO 41
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 41

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 42
<211> LENGTH: 57
<212> TYPE: DNA
<213> ORGANISM: Artificial sequence
<220> FEATURE:
<223> OTHER INFORMATION: Synthetic oligonucleotide

<400> SEQUENCE: 42
atggaatgga gctgggtctt tctcttcttc ctgtcagtaa ctacaggtgt ccactcg         57

<210> SEQ ID NO 43
<211> LENGTH: 19
<212> TYPE: PRT
<213> ORGANISM: Artificial sequence
<220> FEATURE:
<223> OTHER INFORMATION: Synthetic peptide

<400> SEQUENCE: 43

Met Glu Trp Ser Trp Val Phe Leu Phe Phe Leu Ser Val Thr Thr Gly
1               5                   10                  15

Val His Ser

<210> SEQ ID NO 44
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 44
atgagtgtgc ccactcaggt cctggggttg ctgctgctgt ggcttacaga tgccagatgc      60

<210> SEQ ID NO 45
<211> LENGTH: 20
<212> TYPE: PRT
<213> ORGANISM: Artificial Sequence
<220> FEATURE:
<223> OTHER INFORMATION: Synthetic peptide

```
<400> SEQUENCE: 45

Met Ser Val Pro Thr Gln Val Leu Gly Leu Leu Leu Leu Trp Leu Thr
1               5                   10                  15

Asp Ala Arg Cys
            20

<210> SEQ ID NO 46
<211> LENGTH: 16
<212> TYPE: PRT
<213> ORGANISM: Artificial sequence
<220> FEATURE:
<223> OTHER INFORMATION: Synthetic peptide

<400> SEQUENCE: 46

Arg Ser Ser Gln Ser Ile Val His Ser Gly Asn Thr Tyr Leu Glu
1               5                   10                  15

<210> SEQ ID NO 47
<211> LENGTH: 16
<212> TYPE: PRT
<213> ORGANISM: Artificial sequence
<220> FEATURE:
<223> OTHER INFORMATION: Synthetic peptide

<400> SEQUENCE: 47

Arg Ser Ser Gln Ser Ile Val His Ser Thr Gly Asn Thr Tyr Leu Glu
1               5                   10                  15

<210> SEQ ID NO 48
<211> LENGTH: 16
<212> TYPE: PRT
<213> ORGANISM: Artificial sequence
<220> FEATURE:
<223> OTHER INFORMATION: Synthetic peptide

<400> SEQUENCE: 48

Arg Ser Ser Gln Ser Ile Val His Ser Ala Gly Asn Thr Tyr Leu Glu
1               5                   10                  15

<210> SEQ ID NO 49
<211> LENGTH: 16
<212> TYPE: PRT
<213> ORGANISM: Artificial sequence
<220> FEATURE:
<223> OTHER INFORMATION: Synthetic peptide

<400> SEQUENCE: 49

Arg Ser Ser Gln Ser Ile Val His Ser Glu Gly Asn Thr Tyr Leu Glu
1               5                   10                  15

<210> SEQ ID NO 50
<211> LENGTH: 16
<212> TYPE: PRT
<213> ORGANISM: Artificial sequence
<220> FEATURE:
<223> OTHER INFORMATION: Synthetic peptide

<400> SEQUENCE: 50

Arg Ser Ser Gln Ser Ile Val His Ser Asp Gly Asn Thr Tyr Leu Glu
1               5                   10                  15

<210> SEQ ID NO 51
<211> LENGTH: 16
<212> TYPE: PRT
<213> ORGANISM: Artificial sequence
<220> FEATURE:
```

```
<223> OTHER INFORMATION: Synthetic peptide

<400> SEQUENCE: 51

Arg Ser Ser Gln Ser Ile Val His Ser Ser Gly Gln Thr Tyr Leu Glu
1               5                   10                  15

<210> SEQ ID NO 52
<211> LENGTH: 16
<212> TYPE: PRT
<213> ORGANISM: Artificial sequence
<220> FEATURE:
<223> OTHER INFORMATION: Synthetic peptide

<400> SEQUENCE: 52

Arg Ser Ser Gln Ser Ile Val His Ser Ser Gly Ser Thr Tyr Leu Glu
1               5                   10                  15

<210> SEQ ID NO 53
<211> LENGTH: 16
<212> TYPE: PRT
<213> ORGANISM: Artificial sequence
<220> FEATURE:
<223> OTHER INFORMATION: Synthetic peptide

<400> SEQUENCE: 53

Arg Ser Ser Gln Ser Ile Val His Ser Ser Gly Thr Thr Tyr Leu Glu
1               5                   10                  15

<210> SEQ ID NO 54
<211> LENGTH: 16
<212> TYPE: PRT
<213> ORGANISM: Artificial sequence
<220> FEATURE:
<223> OTHER INFORMATION: Synthetic peptide

<400> SEQUENCE: 54

Arg Ser Ser Gln Ser Ile Val His Ser Ser Gly Ala Thr Tyr Leu Glu
1               5                   10                  15

<210> SEQ ID NO 55
<211> LENGTH: 7
<212> TYPE: PRT
<213> ORGANISM: Artificial sequence
<220> FEATURE:
<223> OTHER INFORMATION: Synthetic peptide

<400> SEQUENCE: 55

Lys Ala Ser Gln Arg Phe Ser
1               5

<210> SEQ ID NO 56
<211> LENGTH: 7
<212> TYPE: PRT
<213> ORGANISM: Artificial sequence
<220> FEATURE:
<223> OTHER INFORMATION: Synthetic peptide

<400> SEQUENCE: 56

Lys Ala Ser Ser Arg Phe Ser
1               5

<210> SEQ ID NO 57
<211> LENGTH: 7
<212> TYPE: PRT
<213> ORGANISM: Artificial sequence
<220> FEATURE:
<223> OTHER INFORMATION: Synthetic peptide
```

```
<400> SEQUENCE: 57

Lys Ala Ser Thr Arg Phe Ser
1               5

<210> SEQ ID NO 58
<211> LENGTH: 7
<212> TYPE: PRT
<213> ORGANISM: Artificial sequence
<220> FEATURE:
<223> OTHER INFORMATION: Synthetic peptide

<400> SEQUENCE: 58

Lys Ala Ser Ala Arg Phe Ser
1               5
```